(12) United States Patent
Huber

(10) Patent No.: US 8,381,600 B2
(45) Date of Patent: *Feb. 26, 2013

(54) MEASURING SYSTEM HAVING A MEASURING TRANSDUCER OF VIBRATING-TYPE

(75) Inventor: Christof Huber, Bonn (CH)

(73) Assignee: Endress + Hauser Flowtec AG, Reinach (CH)

( * ) Notice: Subject to any disclaimer, the term of this patent is extended or adjusted under 35 U.S.C. 154(b) by 301 days.

This patent is subject to a terminal disclaimer.

(21) Appl. No.: 12/659,543

(22) Filed: Mar. 12, 2010

(65) Prior Publication Data

US 2010/0257943 A1    Oct. 14, 2010

Related U.S. Application Data

(60) Provisional application No. 61/213,103, filed on May 7, 2009.

(30) Foreign Application Priority Data

Mar. 12, 2009 (DE) .......................... 10 2009 012 474

(51) Int. Cl.
*G01F 1/84* (2006.01)
(52) U.S. Cl. .................................. 73/861.357
(58) Field of Classification Search ............... None
See application file for complete search history.

(56) References Cited

U.S. PATENT DOCUMENTS

| | | | |
|---|---|---|---|
| 5,307,689 A | 5/1994 | Nishiyama et al. | |
| 5,827,979 A | 10/1998 | Schott et al. | |
| 6,199,022 B1 | 3/2001 | Cunningham | |
| 7,325,462 B2 * | 2/2008 | Bitto et al. | 73/861.355 |
| 7,360,451 B2 * | 4/2008 | Bitto et al. | 73/861.355 |
| 7,685,888 B2 * | 3/2010 | Jouwsma et al. | 73/861.355 |
| 2007/0119262 A1 | 5/2007 | Bartstra | |
| 2007/0151370 A1 * | 7/2007 | Bitto et al. | 73/861.357 |
| 2007/0151371 A1 * | 7/2007 | Bitto et al. | 73/861.357 |
| 2008/0141789 A1 | 6/2008 | Kassubek et al. | |
| 2010/0257943 A1 | 10/2010 | Huber | |

FOREIGN PATENT DOCUMENTS

| | | |
|---|---|---|
| DE | 102004026322 | 9/2005 |
| EP | 2034280 | 11/2009 |
| JP | 06331405 | 2/1994 |

OTHER PUBLICATIONS

English translation of the International Preliminary Examination Report.
Search Report issued in accordance with WO Patent Application PCT/EP20 10/052980.

* cited by examiner

*Primary Examiner* — Harshad R Patel
(74) *Attorney, Agent, or Firm* — Bacon & Thomas, PLLC

(57) ABSTRACT

A measuring system comprising a measuring transducer generating primary signals influenced by at least one measured variable characterizing the flowing medium; an evaluating circuit processing primary signals delivered by the measuring transducer to measured values. The measuring transducer includes: at least one measuring tube for conveying medium to be measured; an exciter mechanism acting on the measuring tube for causing the at least one measuring tube to vibrate; and a sensor arrangement for registering oscillations of the measuring tube. The sensor arrangement including first, second and third oscillation sensors spaced from each other for generating first, second, and third primary signals of the measuring transducer, respectively, representing vibrations of the measuring tube. Based on said primary signals the evaluating circuit generates a measured value of mass flow representing a mass flow rate of medium flowing through the measuring transducer.

52 Claims, 4 Drawing Sheets

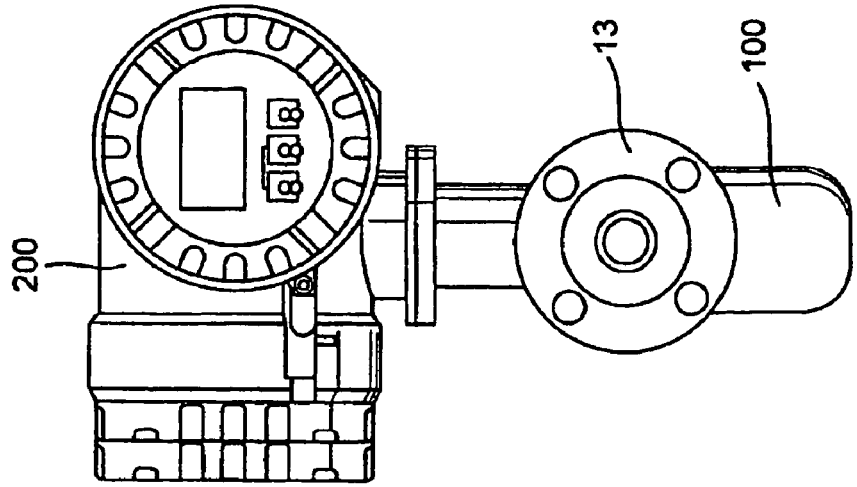
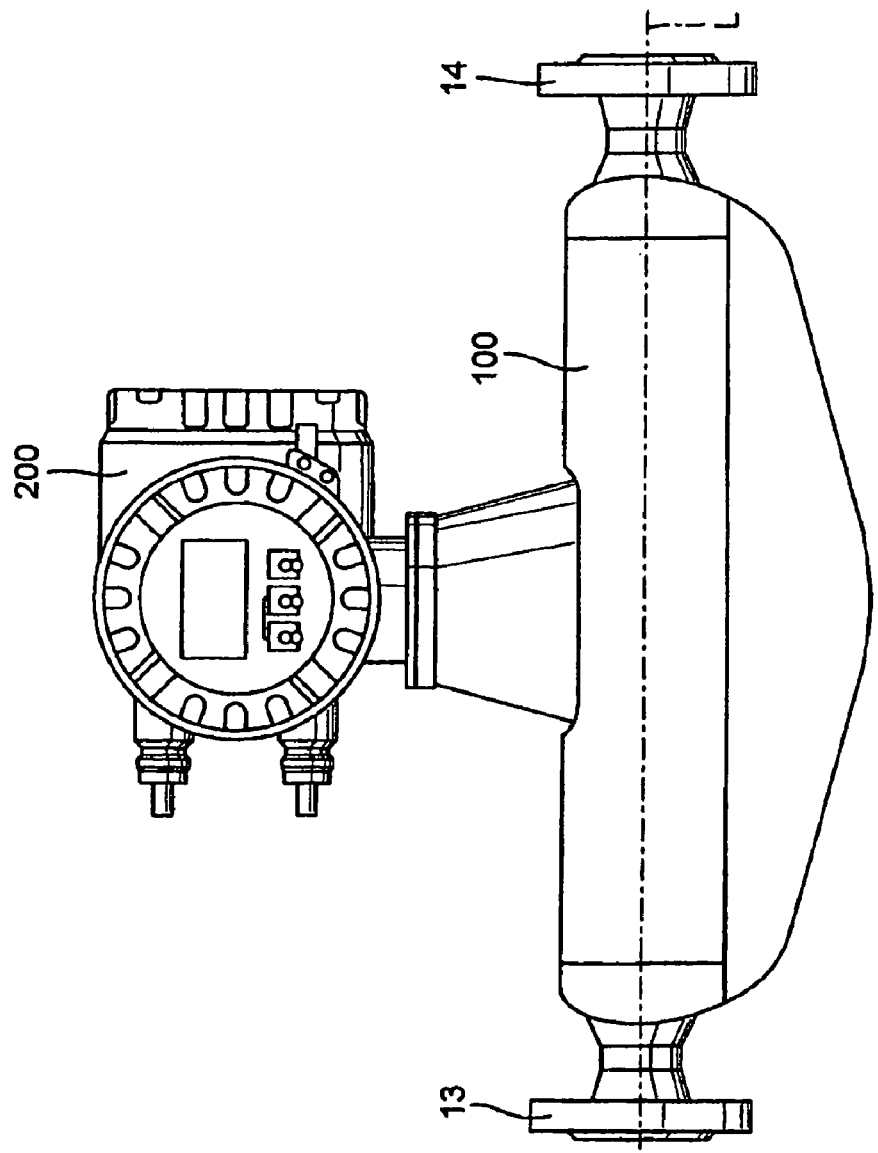

MEASURING SYSTEM HAVING A MEASURING TRANSDUCER OF VIBRATING-TYPE

CROSS-REFERENCE TO RELATED APPLICATION

This application is nonprovisional which claims the benefit of U.S. Provisional Application 61/213,103 filed on May 7, 2009.

TECHNICAL FIELD

The invention relates to a measuring system, especially a measuring system embodied as a compact measuring device and/or a Coriolis, mass flow, measuring device, for flowable, especially fluid, media, which comprises: A measuring transducer of vibration-type, through which a medium flows, at least at times, during operation and which generated primary signals influenced by at least one measured variable characterizing the flowing medium, especially a mass flow, a density, a pressure, a viscosity etc.; as well as an evaluating circuit electrically coupled with the measuring transducer and processing primary signals delivered by the measuring transducer to measured values.

BACKGROUND DISCUSSION

In industrial measurements technology, especially also in connection with the control and monitoring of automated manufacturing processes, for ascertaining characteristic measured variables of media, for example, liquids and/or gases, flowing in a process line, for example, a pipeline, often measuring systems are used, which, by means of a measuring transducer of vibration type and, connected thereto, a driving, and evaluating, electronics (most often accommodated in a separate electronics housing) induce reaction forces, for example, Coriolis forces, in the flowing medium and produce, derived from these, a measurement signal correspondingly representing the at least one measured variable, for example, mass flow, density, viscosity or some other process parameter.

Measuring systems of this kind, which are often formed by means of an inline measuring device in compact construction with integrated measuring transducer, such as, for instance, a Coriolis mass flow meter, have been known for a long time and have proven themselves in industrial use. Examples of such measuring systems having a measuring transducer of vibration type, or also individual components of thereof, are described e.g. in EP-A 317 340, JP-A 8-136311, JP-A 9-015015, US-A 2007/0119264, US-A 2007/0119265, US-A 2007/0151370, US-A 2007/0151371, US-A 2007/0186685, US-A 2008/0034893, US-A 2008/0141789, U.S. Pat. Nos. 4,738,144, 4,777,833, 4,777,833, 4,801,897, 4,823,614, 4,879,911, 5,009,109, 5,024,104, 5,050,439, 5,291,792, 5,398,554, 5,476,013, 5,531,126, 5,602,345, 5,691,485, 5,796,010, 5,796,011, 5,796,012, 5,804,741, 5,869,770, 5,945,609, 5,979,246, 6,047,457, 6,092,429, 6,073,495, 6,311,136, 6,223,605, 6,330,832, 6,397,685, 6,557,422, 6,651,513, 6,666,098, 6,691,583, 6,840,109, 6,883,387, 7,017,424, 7,040,179, 7,073,396, 7,077,014, 7,080,564, 7,216,550, 7,299,699, 7,360,451, 7,392,709, WO-A 00 14 485, WO-A 01 02 816, WO-A 08/013545, WO-A 08/07 7574 or WO-A 99 40 394. Each of the therein illustrated, measuring transducers comprises at least one, essentially straight, or at least one, curved, measuring tube for conveying the medium, which can, in given cases, also be extremely cold or extremely hot.

During operation of the measuring system, the at least one measuring tube is caused to vibrate for the purpose of generating forms of oscillation influenced by the medium flowing through the tube.

For exciting oscillations of the at least one measuring tube, measuring transducers of vibration-type include an exciter mechanism driven during operation by an electrical driver signal, e.g. a controlled electrical current, generated and correspondingly conditioned by the mentioned driver electronics. The exciter mechanism excites the measuring tube, by means of at least one electromechanical oscillation exciter, especially an electrodynamic, oscillation exciter, through which electrical current flows during operation and which acts essentially directly to the measuring tube, to execute bending oscillations in the wanted mode. Furthermore, such measuring transducers include a sensor arrangement with oscillation sensors, especially electrodynamic oscillation sensors, for at least pointwise registering of inlet-side and outlet-side oscillations of the at least one measuring tube, especially those of the Coriolis mode, and for producing electrical sensor signals influenced by the process parameters to be registered, such as, for instance, the mass flow or the density. As, for example, described in U.S. Pat. No. 7,216, 550, in the case of measuring transducers of the type being discussed, in given cases, also the oscillation exciter can, at least at times, be used as oscillation sensor and/or an oscillation sensor can, at least at times, be used as oscillation exciter.

As excited oscillation form—the so-called wanted mode—in the case of measuring transducers with a curved, e.g. U, V, or Ω shaped measuring tube, normally that eigenoscillation form is selected, in which the measuring tube moves in a pendulum-like manner, at least partially at a lowest natural resonance frequency, about a longitudinal axis of the measuring transducer, in the manner of a cantilever fixed at one end, as a result of which mass flow dependent, Coriolis forces are induced in the medium flowing through the measuring tube. These in turn lead to the fact that, superimposed on the excited oscillations of the wanted mode, in the case of curved measuring tubes, thus pendulum-like cantilever oscillations, are bending oscillations of the same frequency corresponding to at least one, also natural, second oscillation form, the so-called Coriolis mode. In the case of measuring transducers with curved measuring tubes, these cantilever oscillations, caused by Coriolis forces, correspond usually with that eigenoscillation form in which the measuring tube also executes rotational oscillations about a vertical axis oriented perpendicularly to the longitudinal axis. In the case of measuring transducers with straight measuring tubes, for the purpose of generating mass flow dependent, Coriolis forces, often a wanted mode is selected in which the measuring tube at least partially executes bending oscillations essentially in a single plane of oscillation, such that the oscillations in the Coriolis mode are formed, accordingly, as bending oscillations coplanar with the oscillations of the wanted mode, and are of the same oscillation frequency.

As a result, of the superimposing of wanted mode and Coriolis mode, the oscillations of the vibrating measuring tube registered by the sensor arrangement at the inlet and outlet sides of the measuring tube have a mass flow dependent, measurable, phase difference. Normally, the measuring tubes of such measuring transducers, e.g. those used in Coriolis mass flow meters, are excited during operation at an instantaneous, natural resonance frequency of the oscillation form selected for the wanted mode, especially at oscillation amplitude controlled to be constant. Since this resonance frequency especially is also dependent on the instantaneous density of the medium, commercially available Coriolis mass flow meters can measure, in addition to mass flow, also the density of media flowing in the measuring tube. Furthermore, it is also possible, as shown for example in U.S. Pat. Nos. 6,651,513 or 7,080,564, using measuring transducers of vibration type, to directly measure viscosity of the medium flowing through the measuring tube, for example based on an exciter power required for exciting the oscillations.

In the case of measuring transducers with two measuring tubes, these are normally linked into the process line via a distributor piece on the inlet side, extending between the measuring tubes and a connecting flange on the inlet side, as well as via a distributor piece on the outlet side, extending between the measuring tubes and a connecting flange on the outlet side. In the case of measuring transducers having a single measuring tube, such normally communicates with the process line via an essentially straight piece of connecting tube which opens into the inlet side of the measuring tube, as well as an essentially straight piece of connecting tube which opens into the outlet side of the measuring tube. Furthermore, each of the illustrated measuring transducers having a single measuring tube includes, composed of a single piece or multiple parts, at least one tubular, box-shaped, or plate-shaped counteroscillator, which, with formation of a first coupling zone, is coupled to the inlet side of the measuring tube, and, with formation of a second coupling zone, is coupled to the outlet side of the measuring tube, and which in operation essentially rests, or oscillates equally and oppositely to the measuring tube, that is, with the same frequency and opposite phase. The inner part of the measuring transducer, formed by measuring tube and counteroscillator, is normally held in a protective, measuring transducer housing alone by means of the two pieces of connecting tube, via which the measuring tube communicates with the process line during operation, especially in a way enabling oscillation of the inner part relative to the measuring tube. In the case of measuring transducers shown in, for example, U.S. Pat. Nos. 5,291,792, 5,796,010, 5,945,609, 7,077,014, US-A 2007/0119264, WO-A 01 02 816, or also WO-A 99 40 394, having a single, essentially straight, measuring tube, the latter and the counteroscillator are oriented essentially coaxially to one another, as is common in conventional measuring transducers. In standard measuring transducers of the previously named type, the counteroscillator normally is also essentially tubular, and is formed as an essentially straight hollow cylinder, which is arranged in the measuring transducer such that the measuring tube is at least partially surrounded by the counteroscillator. Used as materials for such counteroscillators are normally relatively cost-efficient types of steel, such as structural steel, or free-machining steel, especially when titanium, tantalum, or zirconium are used for the measuring tube.

The exciter mechanism of measuring transducers of the type being discussed normally has at least one, usually electrodynamic, magnet assembly, serving as oscillation exciter, and acting differentially on the at least one measuring tube, and the, in given cases, present, counteroscillator, or the, in given cases, present, other measuring tube, while the sensor arrangement includes an inlet-side oscillation sensor, most often also electrodynamic, as well as, on the outlet side, an oscillation sensor of essentially the same construction. Usually, at least the magnet assemblies are essentially of the same construction. Such magnet assemblies serving as oscillation transducers of standard measuring transducers of vibration type are formed by means of a magnetic coil (in the case of measuring transducers with one measuring tube and a counteroscillator coupled thereto, the coil is normally mounted on the latter), as well as by means of an elongated, especially rod-shaped, permanent magnet, which, serving as an armature, interacts with the at least one magnetic coil, especially plunging into the coil, and which is mounted correspondingly to the measuring tube to be vibrated. This has the advantage, for example, that, by means of the magnet assemblies, the oscillatory movements between the vibrating measuring tube and its counterpart, that is, the, in given cases, present counteroscillator or the, in given cases, present, other measuring tube, can be differentially registered, or produced, as the case may be. The permanent magnet and the magnetic coil serving as exciter, or sensor, coil are, in such case, normally oriented essentially coaxially to one another. Additionally, in the case of conventional measuring transducers, the magnet assembly serving as oscillation exciter is normally formed and positioned in the measuring transducer in such a way that it acts essentially centrally on the at least one measuring tube. In such case, the magnet assembly serving as oscillation exciter is, as shown, for example, also in the measuring transducers disclosed in U.S. Pat. Nos. 5,796,010, 6,840,109, 7,077,014 or 7,017,424, usually mounted at least pointwise along an imaginary central peripheral line of the measuring tube on its outer side. Alternatively to oscillation exciters formed by means of a magnet assembly acting centrally and directly to the measuring tube, exciter mechanisms formed, as provided in U.S. Pat. Nos. 6,557,422, 6,092,429 or 4,823,614 among others, for example, by means of two magnet assemblies mounted not in the center of the measuring tube, but, instead, shifted, respectively, toward its inlet and outlet sides, can also be used, or, as provided in U.S. Pat. Nos. 6,223,605 or 5,531,126, among others, exciter mechanisms formed, for example, by means of a magnet assembly working between the, in given cases, present counteroscillator and the measuring transducer housing, are also used.

In the case of most market-ordinary measuring transducers of vibration-type, the oscillation sensors of the sensor arrangement are, such as already indicated, at least to the extent that they work according to the same principle of action, embodied with essentially equal construction to that of the at least one oscillation exciter. Accordingly, also the oscillation sensors of such a sensor arrangement are most often, in each case, formed by means of at least one coil, which is usually affixed to the, in given cases, present counteroscillator and through which, at least at times, a variable magnetic field passes, and, associated therewith, at least at times, supplied with an induced measurement voltage, as well as a magnetic armature, which is permanently affixed to the measuring tube and delivers the magnetic field interacting with the at least one coil. Each of the aforementioned coils is, moreover, connected with the mentioned operating, and evaluating, electronics of the in-line measuring devices by means of at least one pair of electrical connecting lines, which most often are led on an as short as possible paths from the coils via the counteroscillator to the transducer housing.

As, among other things, discussed in the initially mentioned US-A 2008/0141789, U.S. Pat. Nos. 6,920,798, 5,731,527, 7,318,356, 6,868,740, 6,758,102, 5,301,557, 5,576,500, or 5,734,112, measuring transducers of vibration-type and, insofar, the entire therewith formed measuring system can have, besides the initially mentioned sensitivity to the primary measured variables, mass flow rate or density and, in given cases, also viscosity, also a certain cross sensitivity to pressure, this, especially, also in the case, in which the medium has two, or more, phases, for instance, in the case of a mixture of liquid and gas. This pressure sensitivity can lead, at times, to a, when also slight, but, because of the desired high accuracy of measurement, nevertheless not directly disregardable corruption of the primary measured value, such as, for instance, the mass flow, and compensating measures corresponding to the measuring errors can be required.

An opportunity for counteracting the pressure sensitivity of measuring systems of the type being discussed can, such as provided e.g. in U.S. Pat. Nos. 6,920,798, 5,731,527 or 5,301,557, be to reduce the cross sensitivity of the measuring transducer with mechanical means, such as, for instance, metal rings encircling the measuring tube coaxially or ceramic windings or through application of comparatively thick walled, measuring tubes. Conversely, such as, for example, also provided in US-A 2008/0034893, the pressure sensitivity of the measuring transducer can, in advantageous manner, however, also be utilized to register the pressure intentionally as another measured variable of the measuring system formed by means of the measuring transducer, and, based thereon, to perform a measurement error compensation. Alternatively thereto or in supplementation thereof, the pressure supplementally ascertained by means of the measuring transducer can also be output in the form of validated measured values of the measuring system, used for a measuring system internal, self-diagnosis of the measuring system and/or applied for monitoring predetermined qualities of the medium. The ascertaining the pressure can be implemented, in the case of conventional Coriolis, mass flow measuring devices, for example, by means of strain gages, which, such as provided in US-A 2008/0141789 or U.S. Pat. No. 6,868,740, are placed on the at least one measuring tube or on one of the mentioned connecting tube pieces, and/or, such as, for example, shown in U.S. Pat. Nos. 7,318,356, 5,576,500 or 5,734,112, by means of multimodal exciting of the measuring tube as well as by physical mathematical models furnished in the evaluating circuit.

A disadvantage of the solutions known from the state of the art for pressure measurement by means of measuring transducers of vibration-type is, however, to be seen in the fact that they are not always exact enough for a highly precise, largely pressure independent, or pressure compensated, measuring of the mass flow, e.g. the mass flow rate, or that, supplementally to the unavoidable, corresponding modifying of the evaluating circuit, yet additional sensors, of different kind in comparison to the primary oscillation sensors, such as, for instance, strain gages, must be used and must be affixed directly on measuring tube segments assuming the temperature of the medium and, in given cases, vibrating, or that correspondingly modified exciter mechanisms and/or correspondingly modified driver electronics must be used. Associated therewith, both experimental effort for calibrating such measuring systems as well as also an increased test effort for the purpose of assuring the durability of the additional sensors and/or electronic components can be expected.

An object of the invention is, consequently, to improve measuring systems formed by means of measuring transducers of vibration-type toward the goal of enabling therewith a highly accurate measuring of the mass flow, e.g. the mass flow rate, also in the case of pressure of the through flowing medium fluctuating over a broad range, in given cases, also a sufficiently precise measuring of the pressure itself in the sense of producing validated, measured values, especially, also combined with application of measurements technology proven in such measuring systems, such as, for instance, established oscillation sensors or also technologies and architectures of established evaluating circuits.

For achieving the object, the invention resides in a measuring system for flowable, especially fluid, media, especially a measuring system developed as a compact measuring device and/or a Coriolis, mass flow, measuring device, which measuring system includes a measuring transducer through which a medium flows during operation, at least at times, and which generated primary signals influenced by at least one measured variable characterizing the flowing medium, especially a mass flow, a density, a pressure, a viscosity etc.; as well as an evaluating circuit electrically coupled with the measuring transducer and processing the primary signals delivered by the measuring transducer to measured values. The measuring transducer of the measuring system of the invention includes: At least one measuring tube, for example, a measuring tube at least sectionally curved, vibrating during operation, at least at times, and serving for conveying medium to be measured; an exciter mechanism having at least one oscillation exciter, for example, an electrodynamic, oscillation exciter, acting on the measuring tube for causing the at least one measuring tube to vibrate; as well as a sensor arrangement serving for registering oscillations of the measuring tube and having a first oscillation sensor, for example, an electrodynamic, first oscillation sensor, arranged on the measuring tube, for example, on the inlet side and/or on a side of the measuring tube occupied by the oscillation exciter, and spaced from the at least one oscillation exciter, for delivering a first primary signal of the measuring transducer representing vibrations of the measuring tube; and a second oscillation sensor, for example, an electrodynamic, second oscillation sensor, arranged to the measuring tube, for example, on the outlet side and/or on a side of the measuring tube occupied by the first oscillation sensor, and spaced from the first oscillation sensor, for example, also spaced equally far from the at least one oscillation exciter as the first oscillation sensor, for delivering a second primary signal of the measuring transducer, for example, simultaneously with the first primary signal, representing vibrations of the measuring tube; as well as a third oscillation sensor, for example, an electrodynamic, third oscillation sensor, arranged to the measuring tube, for example, on a side of the measuring tube occupied by the first oscillation sensor, and spaced both from the first oscillation sensor as well as also from the second oscillation sensor, for example, also from the at least one oscillation exciter, for delivering a third primary signal of the measuring transducer, for example, simultaneously with the first primary signal and/or simultaneously with the second primary signal, representing vibrations of the measuring tube. Additionally, the evaluating circuit of the measuring system of the invention generated, at least at times, both by means of the first primary signal as well as also by means of the second primary signal as well as by means of the third primary signal, for example, based on a phase difference existing between the first primary signal and the second primary signal and/or based on a phase difference existing between the third primary signal and another of the primary signals, a measured value of mass flow, for example, a digital, measured value of mass flow, which represents, instantaneously, a mass flow rate, m, of medium flowing through the measuring transducer. Alternatively or in supplementation, it is additionally provided, that the evaluating circuit, at least at times, both by means of the first primary signal as well as also by means of the second primary signal as well as by means of the third primary signal, for example, based on a phase difference existing between the first primary signal and the second primary signal and/or based on a phase difference existing between the first primary signal and the third primary signal, generated a pressure measured value, for example, a digital, pressure measured value, which represents, instantaneously, a pressure, p, in medium flowing through the measuring transducer, for example, a static pressure reigning in the at least one measuring tube.

According to a first embodiment of the invention, it is additionally provided, that the third oscillation sensor is placed on a measuring tube segment of the measuring tube extending between the first oscillation sensor and the at least one oscillation exciter.

According to a second embodiment of the invention, it is additionally provided, that the evaluating circuit recurringly during operation produces a phase difference value of first type, which represents, instantaneously, the phase difference, $\Delta\phi^I$, existing between the first primary signal and the second primary signal.

According to a third embodiment of the invention, it is additionally provided, that the evaluating circuit recurringly during operation produces a phase difference value of second type, which represents, instantaneously, the phase difference, $\Delta\phi^{II}$, existing between the third primary signal and another of the primary signals.

According to a fourth embodiment of the invention, it is additionally provided, that the evaluating circuit, by means of the first primary signal as well as at least one other of the primary signals of the measuring transducer, for example, the second primary signal, produces an interimly representing and/or not sufficiently exactly representing and/or digital, provisional measured value of mass flow of first type, for example, a provisional mass flow, m, of medium flowing through the measuring transducer, for example, based on a phase difference, $\Delta\phi^I$, existing between the first primary signal and the second primary signal. Developing this embodiment of the invention, further, it is additionally provided, that the evaluating circuit generates the provisional measured value of mass flow of first type based on the phase difference, $\Delta\phi^I$, of first type existing between the first primary signal and the second primary signal as well as with application of a measuring system parameter, for example, an experimentally earlier ascertained and/or internally stored, measuring system parameter, representing a first zero point, $ZERO^I$, of the measuring system, and with application of a, for example, experimentally earlier ascertained and/or internally stored, measuring system parameter representing a first sensitivity, $SPAN^I$, of the measuring system. The measuring system parameter representing the first zero point, $ZERO^I$, of the measuring system can correspond especially to a phase difference, $\Delta\phi^I_0$, measured between the first primary signal and the second primary signal, in the case of medium standing in the measuring tube, i.e. $m_{DESIRED}=0$, and/or to an provisional measured value of mass flow of first type ascertained in the case of medium standing in the measuring tube, i.e. $m_{DESIRED}=0$. The measuring system parameter representing the first sensitivity, $SPAN^I$, of the measuring system can, in turn, correspond to a phase difference, $\Delta\phi^I_1$, measured between the first primary signal and the second primary signal in the case of supplying the measuring transducer with a flowing medium of known and/or impressed, mass flow rate, $m_{DESIRED}< >0$, and/or a rate ascertained by means of a reference, mass flow measuring device and/or to a phase difference value of first type ascertained in the case of supplying the measuring transducer with a flowing medium of known and/or impressed, mass flow rate, $m_{DESIRED}< >0$, and/or also to a phase difference, $\Delta\phi^I_1$, in the case of supplying the measuring transducer with a flowing medium also of known, average static pressure, $p_{DESIRED1}>0$, measured between the first primary signal and the second primary signal, for example, an impressed, average static pressure and/or an average static pressure ascertained by means of a reference, pressure measuring device.

According to a fifth embodiment of the invention, it is additionally provided, that the evaluating circuit produces, by means of the third primary signal as well as at least one other of the primary signals of the measuring transducer, for example, the first primary signal and/or the second primary signal, a provisional measured value of mass flow of second type, for example, one interimly and/or not sufficiently exactly representing a mass flow, m, of medium flowing through the measuring transducer, and/or a digital one, for example, one based on a phase difference, $\Delta\phi^{II}$, existing between the third primary signal and another of the primary signals. Developing this embodiment of the invention, further, it is additionally provided, that the evaluating circuit generates the provisional measured value of mass flow of second type based on a phase difference, $\Delta\phi^{II}$, of second type existing between the third primary signal and another of the primary signals as well as with application of a measuring system parameter, for example, an experimentally earlier ascertained and/or internally stored, measuring system parameter, representing a second zero point, $ZERO^{II}$, of the measuring system and with application of a measuring system parameter, for example, an experimentally earlier ascertained and/or internally stored, measuring system parameter, representing a second sensitivity, $SPAN^{II}$, of the measuring system. The measuring system parameter representing the second zero point, $ZERO^{II}$, of the measuring system can correspond especially to a phase difference, $\Delta\phi^{II}_0$, measured between the third primary signal and another of the primary signals in the case of medium standing in the measuring tube, i.e. $m_{DESIRED}=0$, and/or correspond to a provisional measured value of mass flow of second type ascertained in the case of medium standing in the measuring tube, i.e. $m_{DESIRED}=0$. The measuring system parameter representing the second sensitivity, $SPAN^{II}$, of the measuring system can, in turn, correspond to a phase difference, $\Delta\phi^{II}_1$, between the third primary signal and another of the primary signals, measured in the case of supplying the measuring transducer with a flowing medium of known mass flow rate, $m_{DESIRED}< >0$, for example, an impressed one and/or one ascertained by means of a reference, mass flow measuring device, and/or to a phase difference value of second type ascertained in the case of supplying the measuring transducer with a flowing medium of known mass flow rate, $m_{DESIRED}< >0$, for example, an impressed one and/or one ascertained by means of a reference, mass flow measuring device, and/or also to a phase difference, $\Delta\phi^{II}_1$, between the third primary signal and another of the primary signals, measured in the case of supplying the measuring transducer with a flowing medium also of known, average static pressure, $p_{DESIRED1}>0$, for example, an impressed one and/or one ascertained by means of a reference, pressure measuring device.

According to a sixth embodiment of the invention, it is additionally provided, that the evaluating circuit generates the measured value of mass flow with application of a measuring system parameter, for example, an experimentally earlier ascertained and/or internally stored, measuring system parameter, representing a relative pressure dependence, $PRESSURE^I$, of the first sensitivity, $SPAN^I$, of the measuring system referenced, for example, to the first sensitivity, $SPAN^I$, of the measuring system and/or that the evaluating circuit generates the measured value of mass flow with application of a measuring system parameter, for example, an experimentally earlier ascertained and/or internally stored, measuring system parameter, representing a relative pressure dependence, $PRESSURE^{II}$, of the second sensitivity, $SPAN^{II}$, of the measuring system referenced, for example, to the second sensitivity, $SPAN^{II}$, of the measuring system.

The measuring system parameter representing the pressure dependence, $PRESSURE^I$, of the first sensitivity, $SPAN^I$, of the measuring system can be ascertained based on a phase difference, $\Delta\phi^I_{p1}$, measured between the first primary signal and the second primary signal in the case of supplying the measuring transducer with a flowing medium of known first average static pressure, $p_{DESIRED1}$, for example, an impressed one and/or one ascertained by means of a reference, pressure measuring device, and based on a phase difference, $\Delta\phi^I_{p2}$, measured between the first primary signal and the second primary signal in the case of supplying the measuring transducer with a flowing medium of known, second average static pressure, $p_{DESIRED2}$, for example, an impressed one and/or one ascertained by means of a reference, pressure measuring device, for example, also with application of the evaluating circuit. Additionally, the measuring system parameter representing the pressure dependence, $PRESSURE^I$, of the first sensitivity, $SPAN^I$, of the measuring system can be ascertained based on a provisional measured value of mass flow of first type generated in the case of supplying the measuring transducer with a flowing medium of known and/or impressed, first average static pressure, $p_{DESIRED1}$, and/or by means of a first average static pressure, $p_{DESIRED1}$, ascertained by a reference, pressure measuring device, and based on a provisional measured value of mass flow of first type generated in the case of supplying the measuring transducer with a flowing medium of known and/or impressed, second average static pressure, $p_{DESIRED2}$, and/or a second average static pressure, $p_{DESIRED2}$, ascertained by means of a reference, pressure measuring device, for example, also with application of the evaluating circuit.

The measuring system parameter representing the pressure dependence, $PRESSURE^{II}$, of the second sensitivity, $SPAN^{II}$, of the measuring system can, in turn, be ascertained based on a phase difference, $\Delta\phi^{II}_{p1}$, measured between the third primary signal and another of the primary signals in the case of supplying the measuring transducer with a flowing medium of known, first average static pressure, $p_{DESIRED1}$, for example, an impressed one and/or one ascertained by means of a reference, pressure measuring device and based on a phase difference, $\Delta\phi^{II}_{p2}$, measured between the third primary signal and another of the primary signals in the case of supplying the measuring transducer with a flowing medium of known, second average static pressure, $p_{DESIRED2}$, for example, an impressed one and/or one ascertained by means of a reference, pressure measuring device, for example, also with application of the evaluating circuit. Additionally, the measuring system parameter representing the pressure dependence, $PRESSURE^{II}$, of the second sensitivity, $SPAN^{II}$, of the measuring system can also be ascertained based on a provisional measured value of mass flow of second type generated in the case of supplying the measuring transducer with a flowing medium of known, first average static pressure, $p_{DESIRED1}$, for example, an impressed one and/or one ascertained by means of a reference, pressure measuring device, and based on a provisional measured value of mass flow of second type generated in the case of supplying the measuring transducer with a flowing medium of known, second average static pressure, $p_{DESIRED2}$, for example, an impressed one and/or one ascertained by means of a reference, pressure measuring device, for example, also with application of the evaluating circuit.

According to a seventh embodiment of the invention, it is additionally provided, that the evaluating circuit produces during operation, recurringly, a phase difference value of first type, which represents, instantaneously, the phase difference, $\Delta\phi^I$, existing between the first primary signal and the second primary signal, as well as a phase difference value of second type, which represents, instantaneously, the phase difference, $\Delta\phi^{II}$, existing between the third primary signal and another of the primary signals type, and that the evaluating circuit generates the measured value of mass flow and/or the measured value of pressure by means of the phase difference value of first type and by means of the phase difference value of second type.

According to an eighth embodiment of the invention, it is additionally provided, that the evaluating circuit produces, by means of the first primary signal as well as at least one other of the primary signals of the measuring transducer, for example, the second primary signal, a interimly and/or not sufficiently exactly representing of an instantaneous mass flow rate, m, of medium flowing through the measuring transducer and/or a digital, provisional measured value of mass flow of first type, for example, based on a phase difference, $\Delta\phi^I$, existing between the first primary signal and the second primary signal, and that the evaluating circuit produces, by means of the third primary signal as well as at least one other of the primary signals of the measuring transducer, for example, the first primary signal and/or the second primary signal, a provisional measured value of mass flow of second type interimly and/or not sufficiently exactly representing of an instantaneous mass flow rate, m, of medium flowing through the measuring transducer and/or a digital, provisional measured value of mass flow of second type, for example, a provisional measured value of mass flow of second type based on a phase difference, $\Delta\phi^{II}$, existing between the third primary signal and another of the primary signals. Developing this embodiment of the invention further, it is additionally provided, that the evaluating circuit generates the measured value of mass flow and/or the measured value of pressure, in each case, by means of the provisional measured value of mass flow of first type and by means of the provisional measured value of mass flow of second type.

According to a ninth embodiment of the invention, it is additionally provided, that the first oscillation sensor and the third oscillation sensor are so placed in the measuring transducer, that an amplitude of the first primary signal is influenced in smaller measure by an average static pressure reigning instantaneously in the at least one measuring tube than is an amplitude of the third primary signal.

According to a tenth embodiment of the invention, it is additionally provided, that the second oscillation sensor and the third oscillation sensor are so placed in the measuring transducer, that an amplitude of the second primary signal is influenced in smaller measure by an average static pressure reigning instantaneously in the at least one measuring tube than is an amplitude of the third primary signal.

According to an eleventh embodiment of the invention, it is additionally provided, that the first oscillation sensor and the second oscillation sensor are so placed in the measuring transducer, that an amplitude of the first primary signal and an amplitude of the second primary signal are influenced in equal measure by an average static pressure reigning instantaneously in the at least one measuring tube.

According to a twelfth embodiment of the invention, it is additionally provided, that the at least one measuring tube is embodied at least sectionally essentially with V shape.

According to a thirteenth embodiment of the invention, it is additionally provided, that the at least one measuring tube is embodied at least sectionally essentially U shape.

According to a fourteenth embodiment of the invention, it is additionally provided, that at least the first oscillation sensor and the second oscillation sensor are of equal construction relative to one another.

According to a fifteenth embodiment of the invention, it is additionally provided, that at least the first oscillation sensor and the third oscillation sensor are of equal construction relative to one another.

According to a sixteenth embodiment of the invention, it is additionally provided, that the first oscillation sensor is arranged on the inlet side and the second oscillation sensor on the outlet side of the at least one measuring tube.

According to a seventeenth embodiment of the invention, it is additionally provided, that the at least one measuring tube has a measuring tube segment, for example, an at least sectionally curved, measuring tube segment, extending essentially freely oscillating, between an end of the measuring tube defining an inlet-side, oscillation node of oscillations of the measuring tube and an end of the measuring tube defining an outlet-side, oscillation node of oscillations. Additionally, it is, in such case, provided, that both the first oscillation sensor, as well as also the second oscillation sensor, as well as also the third oscillation sensor are so placed in the measuring transducer, that each of the three oscillation sensors registers, for example, predominantly or exclusively, vibrations of the essentially freely oscillating measuring tube segment and/or that the at least one measuring tube is excited during operation by means of the exciter mechanism, at least at times, in a wanted mode, in which it executes, for example, predominantly or exclusively, bending oscillations about an imaginary, oscillation axis, for example, one parallel to or coincident with a longitudinal axis of the measuring transducer, imaginarily connecting ends of the at least one measuring tube, for example, with a single and/or with a lowest resonance frequency, and/or that each of the at least three primary signals of the measuring transducer, for example, primary signals generated simultaneously, has, in each case, a signal component, for example, a dominating signal component and/or a signal component corresponding to the wanted mode, with a signal frequency corresponding to the bending oscillations in the wanted mode and/or to a resonance frequency, for example, a lowest resonance frequency, of the at least one measuring tube.

According to an eighteenth embodiment of the invention, it is additionally provided, that the evaluating circuit generates, at least at times, by means of at least one of the primary signals, a density measured value, for example, a digital, density measured value, which represents, instantaneously, a density, $\rho$, of medium flowing through the measuring transducer.

According to a nineteenth embodiment of the invention, it is additionally provided, that the evaluating circuit generates, at least at times, by means of at least one of the primary signals, a viscosity measured value, for example, a digital, viscosity measured value, which represents a viscosity, $\eta$, of medium flowing through the measuring transducer.

According to a first further development of the invention, the measuring system further includes a driver circuit, for example, a driver circuit communicating during operation with the evaluating circuit, electrically coupled with the measuring transducer, and delivering at least one exciter signal controlling its exciter mechanism.

According to a second further development of the invention, the measuring transducer further includes a counteroscillator, for example, a counteroscillator oscillating during operation essentially with opposite phase to that of the measuring tube and/or a counteroscillator parallel to the measuring tube, affixed to the measuring tube to form a first coupling zone on the inlet side of the measuring tube and to form a second coupling zone on the outlet side of the measuring tube. Additionally, it is, in such case, provided, that both the first oscillation sensor, as well as also the second oscillation sensor, as well as also the third oscillation sensor are so placed in the measuring transducer, that each of the three oscillation sensors, for example, predominantly or exclusively, registers, for example, differentially, oscillations of the at least one measuring tube relative to the counteroscillator; and/or that measuring tube and counteroscillator oscillate with opposite phase relative to one another, during operation, at least at one, shared, oscillation frequency; and/or that both the first primary signal as well as also the second primary signal as well as also the third primary signal represent, for example, opposite-equal, oscillatory movements of the at least one measuring tube relative to the counteroscillator; and/or that the oscillation sensors, for example, equally-constructed, oscillation sensors, register, for example, simultaneously and/or differentially, vibrations of the at least one measuring tube, for example, a U shaped or V shaped, measuring tube, and the counteroscillator, for example, a U shaped or V shaped counteroscillator.

According to a third further development of the invention, the sensor arrangement further includes, for example, an electrodynamic, fourth oscillation sensor arranged on the measuring tube and spaced both from the first oscillation sensor as well as also from the second oscillation sensor as well as also from the third oscillation sensor, for example, also equally far as the third oscillation sensor is from the at least one oscillation exciter, for example, arranged on a side of the measuring tube occupied by the first oscillation sensor and/or by the second oscillation sensor and/or by the third oscillation sensor, which delivers, especially simultaneously with the first and second primary signals and/or simultaneously with the third primary signal, a fourth primary signal of the measuring transducer representing vibrations of the measuring tube.

According to a first embodiment of the third further development, it is, in the case of the measuring system of the invention, additionally provided, that the evaluating circuit generates the measured value of mass flow also by means of the fourth primary signal.

According to a first embodiment of the third further development, it is, in the case of the measuring system of the invention, additionally provided, that at least the third oscillation sensor and the fourth oscillation sensor are of equal construction relative to one another.

According to a first embodiment of the third further development, it is, in the case of the measuring system of the invention, additionally provided, that the third oscillation sensor is arranged on the inlet side and the fourth oscillation sensor on the outlet side of the at least one measuring tube.

According to a first embodiment of the third further development, it is, in the case of the measuring system of the invention, additionally provided, that the third oscillation sensor and the fourth oscillation sensor are so placed in the measuring transducer, that an amplitude of the third primary signal and an amplitude of the fourth primary signal are influenced in equal measure by an internal pressure reigning in the at least one measuring tube.

According to a first embodiment of the third further development, it is, in the case of the measuring system of the invention, additionally provided, that the fourth oscillation sensor is placed on a measuring tube segment of the measuring tube extending between the second oscillation sensor and the at least one oscillation exciter.

According to a first embodiment of the third further development, it is, in the case of the measuring system of the invention, additionally provided, that the evaluating circuit recurringly during operation produces a phase difference value of second type, which represents, instantaneously, the phase difference, $\Delta\phi''$, type existing between the third primary signal and another of the primary signals, and that the phase difference value of second type represents the phase difference, $\Delta\phi^H$, existing between the third primary signal and the fourth primary signal (s4).

According to a first embodiment of the third further development, it is, in the case of the measuring system of the invention, additionally provided, that the evaluating circuit, by means of the third primary signal as well as at least one other of the primary signals of the measuring transducer, for example, the first primary signal and/or the second primary signal, produces, for example, based on a phase difference, $\Delta\phi^H$, existing between the third primary signal and another of the primary signals, a provisional measured value of mass flow of second type, for example, one interimly and/or not sufficiently exactly representing a mass flow, m, of medium flowing through the measuring transducer and/or a digital one, and that the evaluating circuit generates the provisional measured value of mass flow of second type both by means of the third primary signal as well as also by means of the fourth primary signal, for example, based on a phase difference, $\Delta\phi^H$, existing between the third primary signal and the fourth primary signal.

A basic idea of the invention is to register the different influences of pressure reigning in the flowing medium for the individual, mutually spaced, oscillation sensors, and, associated therewith, the cross sensitivities of the sensor arrangement, or the measuring transducer, on pressure during operation as a function of the location of installation the respective oscillation sensors and, among other things, in a manner compensating the influence of pressure on the measured mass flow. Alternatively thereto or in supplementation thereof, the site dependence of the cross sensitivity of the sensor arrangement, or the measuring transducer, on pressure can also be used to register the pressure, as such, by means of measuring transducers of vibration-type, or the therewith produced, primary signals representing measuring tube oscillations.

BRIEF DESCRIPTION OF THE DRAWINGS

The invention, as well as other advantageous embodiments thereof, will now be explained in greater detail on the basis of examples of embodiments presented in the figures of the drawing. Equal parts are provided in all figures with equal reference characters; when it is required to avoid clutter or when it otherwise appears sensible, already mentioned reference characters are omitted in subsequent figures. Other advantageous embodiments or further developments, especially also combinations of initially only individually explained aspects of the invention, will become evident additionally from the figures of the drawing, as well as also from the dependent claims per se. The figures of the drawing show as follows:

FIGS. 1a and b show in different side views, a measuring system embodied as a compact measuring device for media flowing in pipelines;

Figure 2:
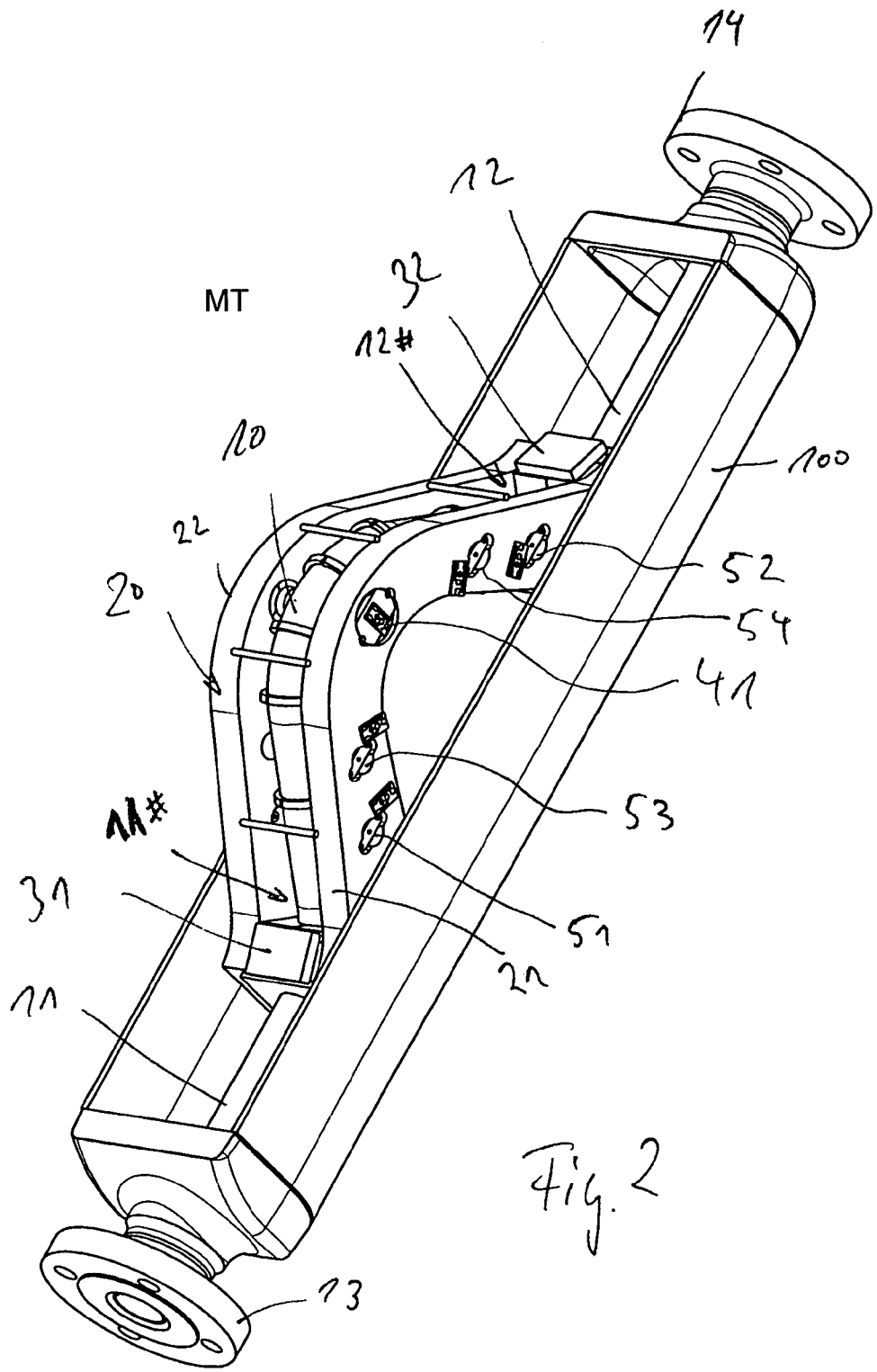
FIG. 2 shows in perspective view, a measuring transducer of vibration-type suited for a measuring system according to FIGS. 1a, 1b.

DETAILED DISCUSSION IN CONJUNCTION
WITH THE DRAWINGS

Presented in FIGS. 1a, 1b as well as 4, is a measuring system insertable in a process line (not shown), for instance, a pipeline of an industrial plant, for example, a measuring system in the form of a Coriolis, mass flow measuring device, density measuring device, viscosity measuring device or the like, serving for measuring and/or monitoring at least one physical, measured variable, for example, a mass flow, a density, a viscosity, a pressure etc., of a medium flowing in the process line. The measuring system, embodied here in the form of an in-line measuring device in compact construction, includes therefor a measuring transducer MT of vibration-type connected via an inlet end as well as an outlet end into the process line. During operation, the medium to be measured, such as, for instance, a low viscosity liquid or a high viscosity paste, or the like, flows through the measuring transducer MT, which, especially during operation, is connected to a measuring device electronics ME of the measuring system. Measuring device electronics ME is supplied with electrical energy externally via connecting cable and/or by means of an internal energy storer. Measuring device electronics ME includes a driver circuit Exc serving for driving the measuring transducer as well as an evaluating circuit μC for processing primary signals of the measuring transducer. Especially, the measuring device electronics ME is formed by means of a microcomputer and/or is in communication with the driver circuit Exc during operation. During operation, the measuring device electronics ME delivers measured values representing at least one measured variable, such as e.g. the instantaneous or integrated mass flow rate. The driver circuit and the evaluating circuit μC, as well as other electronic components of the measuring device electronics serving for the operation of the measuring system, such as, for instance, internal energy supply circuits NRG for providing internal supply voltages $U_N$ and/or communication circuits COM serving for connection to a superordinated, measurement data, processing system and/or a fieldbus, are, additionally, accommodated in a corresponding electronics housing 200, especially an electronics housing, which is impact and/or explosion resistant and/or hermetically sealed. For visualizing measuring system, internally produced, measured values and/or, in given cases, measuring system internally generated status reports, such as, for instance, an error report or an alarm, the measuring system can, on-site, furthermore, have a display, and operating, element HMI, communicating, at least at times, with the measuring device electronics, such as, for instance, an LCD, or TFT, display placed in the electronics housing behind a window correspondingly provided therein, as well as a corresponding input keypad and/or a touch screen. In advantageous manner, the measuring device electronics ME, especially a programmable and/or remotely parameterable, measuring device electronics ME, can additionally be so designed, that it can, during operation of the in-line measuring device, exchange with an electronic data processing system superordinated therewith, for example, a programmable logic controller (PLC), a personal computer and/or a work station, via a data transmission system, for example, a fieldbus system and/or wirelessly per radio, measuring, and/or other operating, data, such as, for instance, current measured values or tuning, and/or diagnostic, values serving for control of the inline-measuring device. In such case, the measuring device electronics ME can, for example, be formed by means of an internal energy supply circuit NRG, which is fed during operation via the aforementioned fieldbus system by an external energy supply provided in the data processing system. For the case, in which the in-line measuring device is designed for coupling to a fieldbus, or other, communication system, the measuring device electronics ME can have a corresponding communication interface COM for data communication according to one of the relevant industry standards.

The electrical connecting of the measuring transducer to the aforementioned measuring device electronics can occur by means of corresponding connecting lines, which are led out from the electronics housing 200, for example, via cable feed-through, and extend at least sectionally within the transducer housing. The connecting lines can be embodied, in such case, at least partially as electrical line wires encased, at least sectionally, in an electrical insulation, e.g. in the form of "twisted pair" lines, flat ribbon cables and/or coaxial cables. Alternatively thereto or in supplementation thereof, the connecting lines can, at least sectionally, be formed also by means of conductive traces of a circuit board, especially a flexible circuit board, in given cases, a lacquered circuit board; compare, for this, also the initially mentioned U.S. Pat. Nos. 6,711,958 or 5,349,872.

Figure 3:
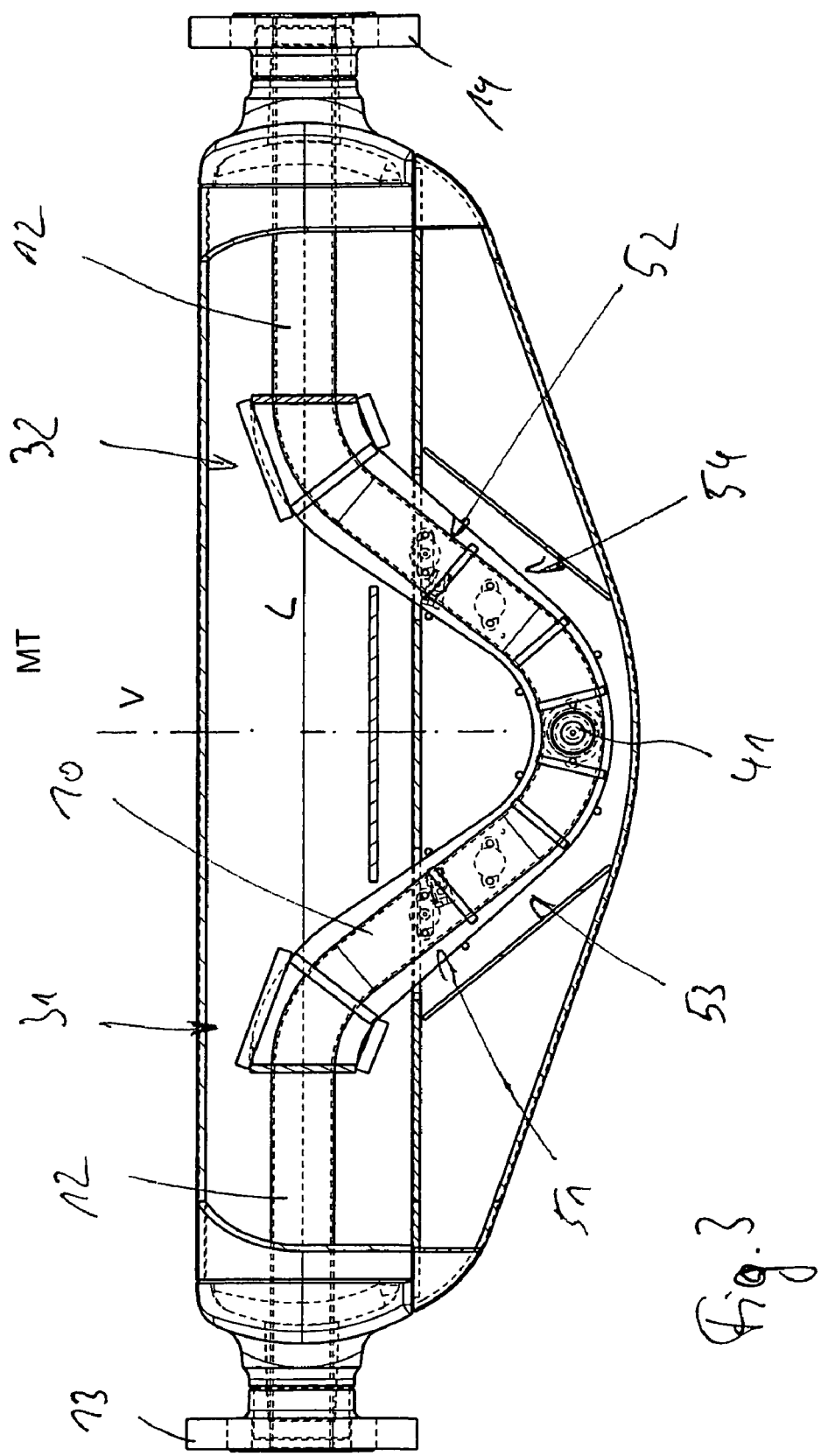
FIG. 3 shows the measuring transducer according to FIG. 2 partially sectioned in a side view.
Figure 4:
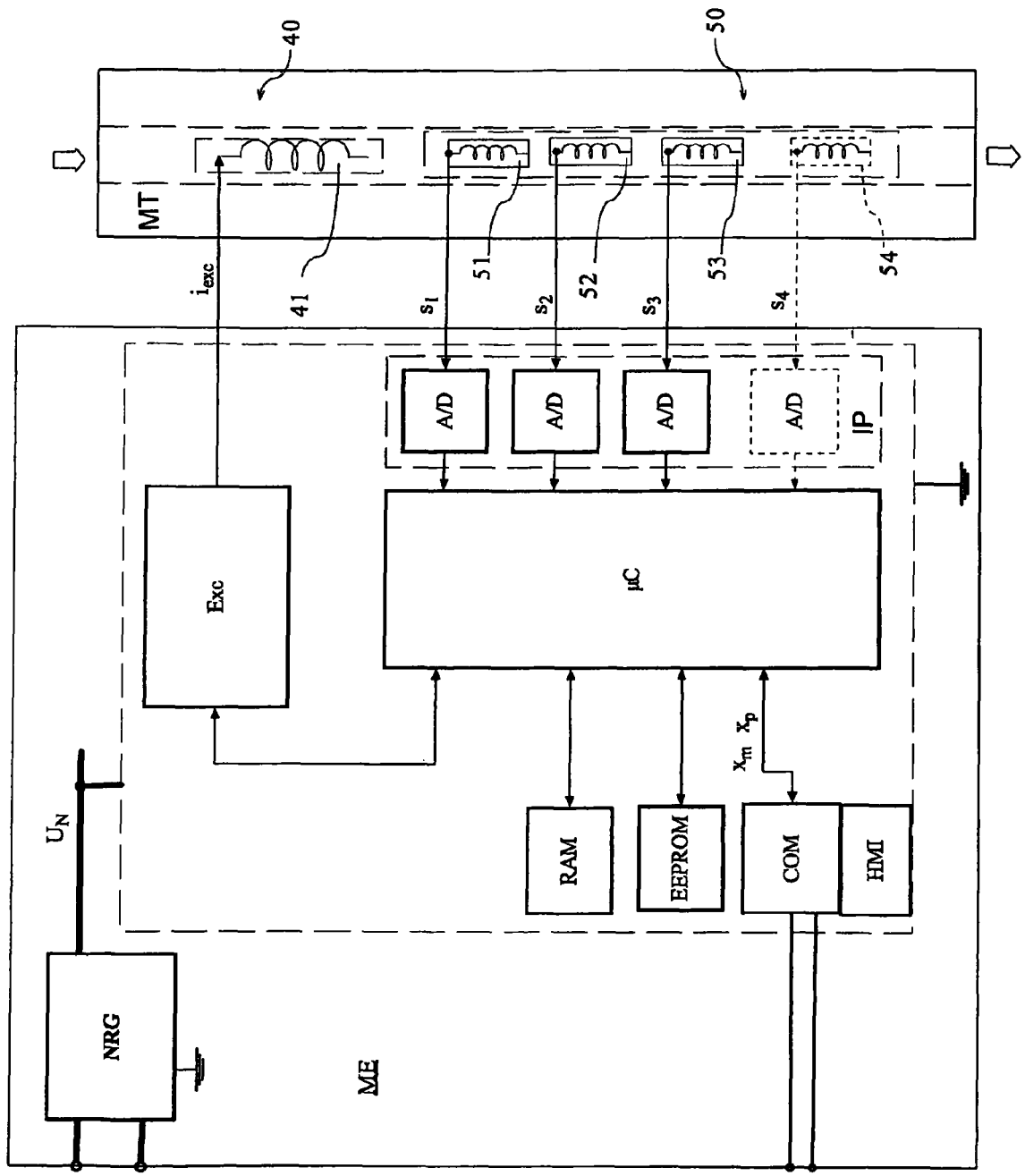
FIG. 4 shows schematically as a type of block diagram, with connected measuring transducers of vibration-type, a measuring device electronics suitable for the measuring system according to FIGS. 1a, 1b.

FIGS. 2 and 3 show schematically a corresponding example of an embodiment for a measuring transducer MT of vibration-type suited for implementing the measuring system of the invention. The measuring transducer MT serves to produce, in a through flowing medium, mechanical reaction forces, e.g. mass flow dependent, Coriolis forces, density dependent, inertial forces and/or viscosity dependent, frictional forces, which react measurably, especially registerably by sensor, on the measuring transducer. Derived from these reaction forces, e.g. a mass flow m, a density ρ and/or a viscosity η of the medium can be measured. The measuring transducer includes therefor a transducer housing 100 as well as an inner part arranged in the transducer housing 100 and effecting the physical-to-electrical transducing of the at least one parameter to be measured.

For conveying the medium, the inner part includes at least one measuring tube 10 (in the example of an embodiment illustrated in FIGS. 2 and 3, a single, at least sectionally curved, measuring tube), which is caused to vibrate during operation, and, in such case, is deformed repeatedly elastically about a static resting position as it oscillates. Here, it is expressly noted, that, although the measuring transducer in the example of an embodiment illustrated in FIGS. 2 and 3 has only a single measuring tube and at least, insofar, resembles, in its mechanical construction, as well as also its principle of action, those measuring transducers proposed in U.S. Pat. Nos. 7,360,451 or 6,666,098, or also those from the assignee under the type designations PROMASS A, PROMASS H, PROMASS P and PROMASS S, for implementing the invention, of course, also measuring transducers with more than one measuring tube can serve, for instance, comparable to the situation in those measuring transducers illustrated in the initially mentioned U.S. Pat. Nos. 5,796,011, 6,311,136, 6,758,102, 5,731,527, 5,301,557 or 6,920,798, or, for example, available from the assignee under the type designations PROMASS E and PROMASS F. In accordance therewith, measuring transducers can also have at least two measuring tubes, for example, measuring tubes mechanically coupled with one another by means of an inlet-side distributor piece and an outlet-side distributor piece and/or by means of at least one inlet-side coupling element and at least one outlet-side coupling element, and/or constructed equally to one another and/or curved and/or parallel relative to one another, for conveying of medium to be measured, which, during operation, for producing the primary signals, vibrate, at least at times, for instance, with equal frequency at a shared oscillation frequency, but, however, with opposite phase relative to one another.

The at least one measuring tube 10 of the measuring transducer and, insofar, also an imaginary centroidal axis of the measuring tube 10 extending within its lumen can, e.g. at least sectionally be embodied essentially with Ω, or U, shape or, such as shown in FIGS. 2 and 3, at least sectionally, essentially with V shape. Since the measuring transducer should be applicable for a number of most varied applications, especially in the area of industrial measuring and automation technology, it is additionally provided, that the measuring tube, depending on application of the measuring transducer, has a diameter, which lies in the range between, for instance, 1 mm and, for instance, 100 mm.

In operation of the measuring transducer, the at least one measuring tube 10 is, such as usual in the case of such measuring transducers, so excited to execute cantilever oscillations at an exciter frequency $f_{exc}$, that it deflects in the so-called wanted mode, about a—here, essentially parallel to or also coincident with an imaginary, longitudinal axis L of the measuring transducer imaginarily connecting the inlet and outlet ends—imaginary bending oscillation axis oscillatingly, essentially according to a natural first eigenoscillation form, especially in such a manner that the at least one measuring tube has an essentially freely oscillating, measuring tube segment (here at least sectionally curved measuring tube segment) extending between an inlet end of the measuring tube defining an inlet-side, oscillation node of oscillations of the measuring tube and an outlet end of the measuring tube defining an outlet-side, oscillation node of oscillations of the measuring tube.

For minimizing of disturbing influences acting on the—in the here illustrated example of an embodiment, single—measuring tube 10, as well as also for reducing of oscillatory energy released on the part of the measuring transducer to the connected process line, in the measuring transducer according to the here illustrated example of an embodiment, furthermore, a counteroscillator 20 is provided. Counteroscillator 20 is, as well as also shown in FIG. 2, arranged laterally spaced in the measuring transducer from the measuring tube 10 and affixed to the measuring tube 10 at each end to form a first coupling zone 11# on the inlet side, essentially defining the aforementioned inlet end of the measuring tube 10, and to form a second coupling zone 12# on the outlet side, essentially defining the aforementioned outlet end of the measuring tube 10. The counteroscillator 20, which, in the illustrated example of an embodiment extends essentially parallel to the measuring tube 10, in given cases, also arranged coaxially with the measuring tube 10, can, for example, be tubular or also essentially box-shaped. For the latter case, the counteroscillator 20 can, as also shown in FIG. 2, or, among other things, also provided in U.S. Pat. No. 7,360,451, be formed, for example, by means of plates arranged on the left and right sides of the measuring tube 10. Alternatively thereto, the counteroscillator 20 can, such as provided, for instance, in U.S. Pat. No. 6,666,098, also be formed by means of a blind tube extending laterally of the measuring tube and parallel thereto.

As evident from a combination of FIGS. 2 and 3, the counteroscillator 20 in the here illustrated example of an embodiment is held by means of at least one inlet-side first coupler 31 on the inlet end 11# of the measuring tube 10 and by means of at least one outlet-side second coupler 32 (especially a second coupler 32 essentially identical to the coupler 31) on the outlet end 12# of the measuring tube 10. Serving as coupler 31, 32 can be, in such case, e.g. simple node plates, which are secured in corresponding manner on the inlet side and on the outlet side, in each case, to the measuring tube 10 and to the counteroscillator 20. Additionally, such as provided in the example of an embodiment illustrated in FIGS. 2 and 3, a completely closed box formed, in each case, by means of node plates, spaced from one another in the direction of the imaginary longitudinal axis L of the measuring transducer, and protruding ends of the counteroscillator 20 at the inlet side and at the outlet side or, in given cases, also a partially open frame can serve as coupler 31, or as coupler 32.

As schematically presented in FIGS. 2 and 3, the measuring tube 10 is additionally correspondingly connected to the process line (not shown) supplying and, respectively, draining the medium via a straight first connecting tube piece 11 opening on the inlet side in the region of the first coupling zone 11# and via a straight second connecting tube piece 12 opening on the outlet side in the region of the second coupling zone 12#, especially a second connecting tube piece 12 essentially identical to the first connecting tube piece 11, wherein an inlet end of the inlet-side connecting tube piece 11 forms essentially the inlet end of the measuring transducer and an outlet end of the outlet-side connecting tube piece 12 forms the outlet end of the measuring transducer. In advantageous manner, the measuring tube 10 and the two connecting tube pieces 11, 12 can be embodied as one piece, so that e.g. a single tubular stock, or semifinished part, can serve for their manufacture. Instead of forming the measuring tube 10, inlet tube piece 11 and outlet tube piece 12, in each case, by segments of a single, one piece tube, these can, in case required, however, also be produced by means of individual, subsequently joined together, e.g. welded together, stock, or semifinished parts. For manufacture of the measuring tube 10, moreover, essentially any of the usual materials for such measuring transducers, such as e.g. steel, Hastelloy, titanium, zirconium, tantalum, etc., can be used.

As furthermore evident from FIGS. 2 and 3, the transducer housing 100, especially a transducer housing 100 bending, and torsion, stiff in comparison to the measuring tube 10, is affixed, especially rigidly, to an, as regards the first coupling zone #11, distal, inlet end of the inlet-side connecting tube piece 11 as well as to a, as regards the first coupling zone #11, distal, outlet end of the outlet-side connecting tube piece 12. As a result, thus, the entire inner part is encased completely, not only by the transducer housing 100, but, also, as a result of its eigenmass and the spring action of both connecting tube pieces 11, 12, also held oscillatably in the transducer housing 100. Additionally to accommodating the inner part, the transducer housing 100 can additionally also serve to hold the electronics housing 200 of the inline-measuring device with therein accommodated driver, and evaluating, circuit. For the case, in which the measuring transducer MT is to be assembled releasably with the process line, for example, a process line in the form of a metal pipeline, there is additionally formed on the inlet-side connecting tube piece 11, on its inlet end, a first connecting flange 13 of the measuring transducer and on the outlet-side connecting tube piece 12, on an outlet end, a second connecting flange 14 of the measuring transducer. The connecting flanges 13, 14 can, in such case, such as quite usual in the case of measuring transducers of the described type, also be integrated at least partially terminally into the transducer housing 100. In case required, the connecting tube pieces 11, 12 can, moreover, however, also be connected directly with the process line, e.g. by means of welding or hard soldering.

In an additional embodiment of the invention, the at least one measuring tube is excited during operation by means of the exciter mechanism, at least at times, in a wanted mode, in which it at least partially—especially predominantly or exclusively—executes bending oscillations about the imaginary oscillation axis connecting inlet, and outlet, ends of the measuring tube imaginarily with one another, for example, with a single and/or a lowest of its resonance frequencies. The bending oscillations of the measuring tube have, in such case, in the region of the inlet-side coupling zone 11# defining the inlet-side end of the measuring tube, an inlet-side, oscillation node and in the region of the outlet-side coupling zone 11# defining the outlet-side end of the measuring tube, an outlet-side, oscillation node, wherein between these two oscillation nodes there extends an essentially freely oscillating tube segment—here corresponding to the actual measuring tube and being at least sectionally curved. In case required, the vibrating measuring tube segment can, however, also, such as, for example, provided in U.S. Pat. No. 7,077,014 or the JP-A 9-015015, be influenced in its oscillatory movements, with targeting, by means of resilient and/or electromotor coupling elements correspondingly supplementally acting on the measuring tube.

In the here illustrated example of an embodiment, the measuring tube 10 executes the bending oscillations relative to counteroscillator 20 and longitudinal axis L, especially at a shared oscillation frequency and with opposite phase relative to one another. In the case of an exciter mechanism acting differentially on measuring tube and counteroscillator, also the counteroscillator 20 is necessarily excited to execute simultaneous cantilever oscillations, and, indeed, such that it oscillates at least partially out of phase, especially essentially with opposite phase, to the measuring tube 10 oscillating in the wanted mode. Especially, measuring tube 10 and counteroscillator 20 are, in such case, additionally so matched to one another, or so excited, that they execute, during operation, at least at times, and at least partially, opposite-equal, thus with equal frequency, however, essentially opposite phase, bending oscillations about the longitudinal axis L. The bending oscillations can, in such case, be so developed, that they are of equal modal order and, thus, at least in the case of resting fluid, essentially equally formed. In other words, measuring tube 10 and counteroscillator 20 move then in the manner of tuning fork tines oscillating relative to one another. According to an additional embodiment of the invention, the exciter, or also wanted, mode, frequency, $f_{exc}$, is, in such case, so set, that it corresponds as exactly as possible to an eigenfrequency, especially a smallest natural eigenfrequency, of bending oscillations of the measuring tube 10. In the case of application of a measuring tube manufactured of stainless steel with a nominal diameter of 29 mm, a wall thickness of, for instance, 1.5 mm, a stretched length of, for instance, 420 mm and a bent length of 305 mm, measured from the inlet end #11 to the outlet end 12#, the lowest resonance frequency of the same, for example, in the case of a density of essentially zero, e.g. in the case of a measuring tube completely filled with air, is about 490 Hz.

For the operationally provided case, in which the medium is flowing in the process line and, thus, the mass flow m is different from zero, Coriolis forces are also induced in the medium by means of the measuring tube 10 vibrating in the above described manner as the medium flows through. These, in turn, react on the measuring tube 10 and effect, so, an additional, by sensor registerable, deformation of the same, essentially according to a natural, second, eigenoscillation form. An instantaneous value of this so-called Coriolis mode superimposed with equal frequency on the excited, wanted mode is, in such case, especially as regards its amplitudes, also dependent on the instantaneous mass flow m—in particular, the mass flow rate. The second eigenoscillation form can, such as usual in the case of such measuring transducers with curved measuring tube, be e.g. the eigenoscillation form of the antisymmetric twist mode, thus that, in the case of which the measuring tube 10, such as already mentioned, also executes rotary oscillations about an imaginary vertical axis V directed perpendicularly to the longitudinal axis L and lying in a single symmetry plane of the illustrated measuring transducer.

The inner part suspended in the transducer housing 100 can additionally also execute pendulum-like oscillations about the longitudinal axis L, in the case of which the coupling zones are rotated about the longitudinal axis and the connecting tube pieces 11, 12 are twisted. In corresponding manner, also the two coupling zones and, thus, also both coupler 31, 32 experience a corresponding torsional twist about the longitudinal axis L, i.e. also they oscillate, and, indeed, relative to one another, essentially with the same phase. In other words, the inner part held oscillatably in the transducer housing has a pendulum-like oscillation mode, in which it moves in a pendulum-like manner, during operation, accompanied by deformations of the two connecting tube pieces 11, 12, at least at times, around the imaginary longitudinal axis L. In such case, the vibrating measuring tube 10 and the counteroscillator 20 supplementally execute shared pendulum-like movements about the longitudinal axis L, which, at least in the case of resting medium, have, relative to one another and to the cantilever oscillations of the counteroscillator 20, essentially the same phase, in case a mass, $m_{20}$, of the counteroscillator 20 is smaller than an instantaneous total mass of the measuring tube 10 conveying the medium. For the reverse case, in which the total mass of the medium conveying measuring tube 10 is smaller than the mass of the counteroscillator 20, these pendulum-like movements of the inner part can have the same phase as the cantilever oscillations of the measuring tube 10.

In the example of an embodiment illustrated in FIGS. 2 and 3, it is additionally provided, that the two connecting tube pieces 11, 12, are so oriented relative to one another as well as relative to an imaginary longitudinal axis L of the measuring transducer imaginarily connecting the two coupling zones 11#, 12#, that the inner part, along with twisting of the two connecting tube pieces 11, 12, can move like a pendulum about the longitudinal axis L. For such purpose, the two connecting tube pieces 11, 12 are to be so oriented relative to one another, that the essentially straight tube segments extend essentially parallel to the imaginary longitudinal axis L, or parallel to the imaginary oscillation axis of the bending oscillations of the measuring tube, such that the tube segments essentially align both with the longitudinal axis L as well as also relative to one another. Since the two connecting tube pieces 11, 12 in the here illustrated example of an embodiment are embodied to be essentially straight over their entire lengths, they are, accordingly, as a whole, oriented essentially aligned relative to one another as well as to the imaginary longitudinal axis L.

For implementing the counteroscillator 20, especially a counteroscillator 20, which is also rather heavy and, at the same time, also rather bending resistant, and for the simplified coordination of the same on measuring tube 10 in the above described manner, such is, in the here illustrated example of an embodiment, formed at least partially by means of plates 21, 22 arranged laterally of the measuring tube 10. In the case of the here illustrated example of an embodiment, the counteroscillator 20 is formed by means of at least two curved, counteroscillator plates 21, 22, of which a first counteroscillator plate 21 is arranged on the left side of the measuring tube 10 and a second counteroscillator plate 22 on the right side of the measuring tube 10. Each of the at least two—here essentially arc, or bow, shaped—counteroscillator plates 21, 22 includes an outer lateral surface, of which a first edge is formed by an, as regards the longitudinal axis, distal, contour giving edge as well as a second edge by an, as regards the longitudinal axis, proximal, contour giving edge. In the example of an embodiment illustrated in FIGS. 2 and 3, additionally each of the at least two counteroscillator plates 21, 22 forming the counteroscillator 20 is arranged essentially parallel to the measuring tube 10. In an additional embodiment of the invention, each of the at least two counteroscillator plates 21, 22, is, furthermore, so embodied and so placed in the measuring transducer relative to the measuring tube 10, that both the distal as well as also the proximal contour giving edge of an each of the at least two counteroscillator plates 21, 22, at least in the region of a midsection of the counteroscillator 20, have a spacing of greater than zero from the longitudinal axis L.

For exciting mechanical oscillations of the measuring tube 10, especially the bending oscillations in the wanted mode, as well as for exciting the, in given cases, present counteroscillator 20, the measuring transducer includes, additionally, an exciter mechanism 40, especially an electrodynamic, exciter mechanism 40. This serves, operated by an exciter signal, e.g. an exciter signal having a controlled electrical current and/or a controlled voltage, delivered from the driver circuit and, in given cases, correspondingly conditioned on the basis of interaction with the evaluating circuit, to convert electrical exciter energy $E_{exc}$ fed by means of the driver circuit into an exciter force $F_{exc}$ acting, e.g. with pulse shape or harmonically, on the measuring tube 10 and deflecting such in the above described manner. The driver circuit can be embodied e.g. in the form of a phase locked loop (PLL), which is used in manner known to those skilled in the art, on the basis of a phase difference, measured between at least one of the oscillation measurement signals s1, s2 and the to be adjusted, or the instantaneously measured, exciter current $i_{exc}$ of the exciter signal, to adjust the exciter frequency, $f_{exc}$, continually, to obtain the instantaneous eigenfrequency of the desired wanted mode. The construction and application of such phase locked loops for driving measuring tubes at one of their mechanical eigenfrequencies is described at length e.g. in U.S. Pat. No. 4,801,897. Of course, also other driver circuits known, per se, to those skilled in the art to be suitable for the tuning the exciter energy $E_{exc}$, can be used, for example, also according to the initially mentioned state of the art, for instance, the initially mentioned U.S. Pat. Nos. 4,777,833, 4,801,897, 4,879,911, 5,009,109, 5,024,104, 5,050,439, 5,804,741, 5,869,770, 6,073,495 or 6,311,136. Additionally, as regards an application of such driver circuits for measuring transducers of vibration-type, reference is made to the measurement transmitters of the series "PROMASS 83", such as available from the assignee, for example, in connection with measuring transducers of the series "PROMASS I". Their driver circuit is, for example, so embodied, that the lateral bending oscillations in the wanted mode are controlled to a constant amplitude, thus an amplitude also largely independent of the density, ρ.

The exciter force $F_{exc}$ can, such as usual in the case of such measuring transducers, be bidirectional or unidirectional and can be tuned, in manner known to those skilled in the art, e.g. by means of an electrical current and/or voltage, control circuit, as regards its amplitude and e.g. by means of a phase locked loop, as regards its frequency. Serving as exciter mechanism 30 can be e.g. an exciter mechanism 40 formed in conventional manner by means of an electrodynamic oscillation exciter 41, for example, a single electrodynamic oscillation exciter 41, acting centrally on the measuring tube. The oscillation exciter 41 can, such as indicated in FIG. 2, be formed, for example, by means of a cylindrical exciter coil, which is secured on the counteroscillator 20 and through which, during operation, a corresponding exciter current flows, and which has, associated therewith, a corresponding magnetic field, as well as a permanently magnetic armature at least partially plunging in the exciter coil, which is affixed externally, especially centrally, to the measuring tube 10. Other exciter mechanisms—also quite suitable for the measuring system of the invention—for driving oscillations of the at least one measuring tube are shown e.g. in the initially mentioned U.S. Pat. Nos. 6,557,422, 6,092,429, 4,823,614, 6,223,605 or 5,531,126. For causing the measuring tube 10 to vibrate, the exciter mechanism is, such as already mentioned, fed by means of a likewise oscillating, exciter signal $i_{exc}$ of adjustable exciter, electrical current amplitude and of adjustable exciter frequency, $f_{exc}$, so that, during operation, a corresponding exciter current flows through the exciter coil of the, here, single, oscillation exciter acting on the measuring tube 10, in order to produce the magnetic field required for moving the measuring tube. The exciter signal, e.g. the exciter current $i_{exc}$, can be formed e.g. harmonically, multifrequently or also rectangularly. The exciter frequency, $f_{exc}$, of the exciter current $i_{exc}$ required for maintaining the bending oscillations of the measuring tube 10, in the case of the measuring transducer illustrated in the example of an embodiment, can, in advantageous manner, be so selected and tuned, that the laterally oscillating measuring tube 10 oscillates essentially in a bending oscillation fundamental mode having a single oscillatory antinode.

For registering oscillations of the measuring tube 10, the measuring transducer additionally includes a corresponding sensor arrangement 50. Such includes, in the case of the measuring system of the invention, a first oscillation sensor 51 arranged on the measuring tube 10, spaced from the at least one oscillation exciter, for example, an electrodynamic, first oscillation sensor 51, for delivering a first primary signal s1, for example, a measurement voltage or a measurement current, representing vibrations of the measuring tube 10, for the measuring transducer, as well as a second oscillation sensor 52 arranged on the measuring tube 10 spaced from the first oscillation sensor 51, especially an electrodynamic, second oscillation sensor 52, which delivers, especially simultaneously with the first primary signal, a second primary signal s2 for the measuring transducer representing vibrations of the measuring tube 10. In the case of the measuring system of the invention, the sensor arrangement additionally includes a third oscillation sensor 53 (especially an electrodynamic, third oscillation sensor 53 and/or a third oscillation sensor 53 constructed equally at least to the first oscillation sensor 51) arranged on the measuring tube 10 spaced at least both from the first oscillation sensor 51 as well as also from the second oscillation sensor 52, especially also from the at least one oscillation exciter, especially on a side of the measuring tube occupied by the first oscillation sensor and/or the second oscillation sensor. This third oscillation sensor 53 delivers, during operation of the measuring transducer, especially simultaneously with the first primary signal s1 and/or simultaneously with the second primary signal s2, a third primary signal s3 likewise representing vibrations of the at least one measuring tube 10. Especially, the sensor arrangement of the measuring system of the invention is so embodied, that both the first primary signal s1, as well as also the second primary signal s2 as well as also the third primary signal s3 represent oscillatory movements of the at least one measuring tube relative to the counteroscillator, especially opposite-equal oscillatory movements—thus, with equal frequency, and opposite phase. The oscillation sensors of the sensor arrangement can, in advantageous manner, additionally be so embodied, that they deliver primary signals of same type, for example, in each case, a signal voltage or a signal current. As quite usual in the case of measuring transducers of vibration-type, at least the first oscillation sensor and the second oscillation sensor are, according to an additional embodiment of the invention, of equal construction relative to one another. Additionally, it can be of advantage, when the first oscillation sensor and the third oscillation sensor are of equal construction relative to one another.

Especially, the at least three oscillation sensors are, in such case, so arranged in the measuring transducer, that both the first oscillation sensor, as well as also the second oscillation sensor, as well as also the third oscillation sensor are so placed in the measuring transducer, that each of the three oscillation sensors, especially predominantly or exclusively, register vibrations of the essentially freely oscillating, measuring tube segment, especially in such a manner that both the first oscillation sensor, as well as also the second oscillation sensor, as well as also the third oscillation sensor are so embodied and so installed in the measuring transducer, that each of the three oscillation sensors, especially predominantly or exclusively, register, especially differentially register, oscillations of the at least one measuring tube relative to the counteroscillator. For the above mentioned case, in which the measuring transducer includes two opposite-equally oscillating measuring tubes, both the first oscillation sensor, as well as also the second oscillation sensor, as well as also the third oscillation sensor are correspondingly so placed in the measuring transducer, that each of the three oscillation sensors, especially predominantly or exclusively, especially simultaneously and/or differentially, registers vibrations, especially opposite-equal oscillations, of both vibrating measuring tubes.

As quite usual in the case of such measuring transducers of vibration-type, used in a measuring system formed as a Coriolis, mass flow, measuring device, the first oscillation sensor 51, according to an embodiment of the invention, additionally, is arranged in the measuring transducer on a side of the measuring tube occupied by the oscillation exciter 41. Furthermore, also the second oscillation sensor 52 can, such as quite usual in the case of such measuring transducers, be arranged in the measuring transducer on the side of the measuring tube occupied by the first oscillation sensor 51, spaced, for example, equally distant from the at least one oscillation exciter, or from the midlength of the measuring tube, as is the first oscillation sensor. Additionally, according to an additional embodiment of the invention, also the third oscillation sensor 53 can be arranged in the measuring transducer on the side of the measuring tube occupied by the first oscillation sensor 51. In case required, the oscillation sensors can, however, be placed, for example, also on a side of the measuring tube lying opposite to the side occupied by the oscillation exciter.

In an additional embodiment of the invention, the first oscillation sensor and the third oscillation sensor are so placed in the measuring transducer, that an amplitude of the first primary signal s1 is influenced in smaller measure by an average static pressure reigning instantaneously in the at least one measuring tube 10, or in the therein guided medium, than is an amplitude of the third primary signal. Alternatively thereto or in supplementation thereof, additionally also the second oscillation sensor and the third oscillation sensor can be so placed relative to one another in the measuring transducer, that an amplitude of the second primary signal s2 is influenced in smaller measure by an average static pressure reigning instantaneously in the at least one measuring tube 10, or in the therein guided medium, than is an amplitude of the third primary signal. Moreover, according to an additional embodiment of the invention, the first oscillation sensor and the second oscillation sensor are so placed in the measuring transducer, that an amplitude of the first primary signal and an amplitude of the second primary signal are influenced in equal measure by an average static pressure reigning instantaneously in the at least one measuring tube.

In the example of an embodiment shown here, the first oscillation sensor 51 is arranged on the inlet side and the second oscillation sensor 52 on the outlet side of the at least one measuring tube 10, especially spaced equally far as the first oscillation sensor from the at least one oscillation exciter, or from the midlength of the measuring tube 10. Additionally, the third oscillation sensor 53 is placed on an measuring tube segment of the measuring tube 10 extending between the first oscillation sensor 51 and the at least one oscillation exciter 41, and, indeed, in each case, spaced both from the first oscillation sensor 51 as well as also from the oscillation exciter 41.

For improving the information content of the primary signals delivered by the sensor arrangement 50, as well as also for increasing the accuracy, with which the therefrom derived measured values are produced during operation by means of the evaluating circuit μC, the sensor arrangement 50, according to a further development of the invention, includes additionally a fourth oscillation sensor 54, especially one constructed equally at least to the third oscillation sensor and/or an electrodynamic one, for delivering a fourth primary signal s4 of the measuring transducer likewise representing vibrations of the measuring tube 10, especially simultaneously with the first and second primary signals and/or simultaneously with the third primary signal. The fourth oscillation sensor 54 as indicated in FIG. 3, is arranged on the measuring tube 10 spaced both from the first oscillation sensor 51 as well as also from the second oscillation sensor 52 as well as also from the third oscillation sensor 52, for example, in turn, on a side of the measuring tube occupied by the first oscillation sensor 51 and/or by the second oscillation sensor 52 and/or by the third oscillation sensor 53. As evident from FIG. 3, in such case, the third oscillation sensor can, for example, be arranged on the inlet side and the fourth oscillation sensor, for example, on the outlet side of the at least one measuring tube 10.

In the example of an embodiment illustrated here for the measuring transducer, also the fourth oscillation sensor is, furthermore, so embodied and so arranged in the measuring transducer, that it, especially predominantly or exclusively, registers, in given cases, also differentially, oscillations of the at least one measuring tube relative to the counteroscillator, especially in such a manner that also the fourth primary signal s4 represents, especially opposite-equally, oscillatory movements of the at least one measuring tube relative to the counteroscillator. For such purpose, the fourth oscillation sensor in the here illustrated example of an embodiment is placed on a measuring tube segment of the measuring tube extending between the second oscillation sensor 52 and the at least one oscillation exciter 41. For the above mentioned case, in which the measuring transducer includes two opposite-equally oscillating measuring tubes, also the fourth oscillation sensor, in turn, is to be so placed in the measuring transducer, that also it, especially predominantly or exclusively, registers opposite-equal oscillations of both vibrating measuring tubes, especially differentially and/or simultaneously with the other oscillation sensors.

In an additional embodiment of the invention, the third oscillation sensor 53 and the fourth oscillation sensor 54 are additionally so arranged in the measuring transducer, that an amplitude of the third primary signal s3 and an amplitude of the fourth primary signal s4 are, for instance, influenced in equal measure by an internal pressure reigning in the at least one measuring tube. This is achieved in the here illustrated example of an embodiment by placing the fourth oscillation sensor on the outlet side on the measuring tube segment of the measuring tube extending between the second oscillation sensor 52 and the at least one oscillation exciter 41 equally far from the at least one oscillation exciter, or of the midlength of the at least one measuring tube, as is the third oscillation sensor arranged on the inlet side on the measuring tube segment of the measuring tube extending between the first oscillation sensor 51 and the at least one oscillation exciter 41.

In an additional embodiment of the invention, both the first oscillation sensor, as well as also the second oscillation sensor, as well as also the third oscillation sensor as well as the, in given cases, present fourth oscillation sensor are, in each case, so placed in the measuring transducer MT, that each of the oscillation sensors, at least predominantly, especially exclusively, registers vibrations of the—here essentially freely oscillating—middle tube segment, and, indeed, in the example of an embodiment illustrated in FIGS. 2 and 3, relative to the counteroscillator 20. As a result, of this, each of the primary signal s1, s2, s3 of the measuring transducer MT has, in each case, a signal component with a signal frequency corresponding to that of the bending oscillations in the wanted mode and/or a resonance frequency, especially a lowest resonance frequency, of the at least one measuring tube 10. Even in the case of application of a rather broadband driver signal, as a result of the high oscillation quality of the measuring transducer MT, it can be assumed, that the signal component of each of the primary signals corresponding to the wanted mode outweighs other signal components, especially signal components corresponding to possible external disturbances and/or classified as noise, and, insofar, is also dominating at least within a frequency range corresponding to a bandwidth of the wanted mode.

The oscillation measurement signals s1, s2, s3, which are delivered by the sensor arrangement and which, in each case, have a signal frequency corresponding to an instantaneous oscillation frequency, $f_{exc}$, of the measuring tube 10 oscillating in the wanted mode, are, such as shown in FIG. 5, fed to the evaluating circuit μC of the measuring device electronics ME, where they are first preprocessed by means of a corresponding input circuit IP, especially preamplified, filtered and digitized, in order then to be able to be suitably evaluated. Serving as input circuit IP, as well as also evaluating circuit μC, can be, in such case, circuit technologies already applied and established in conventional Coriolis, mass flow, measuring devices for the purpose of converting the primary signals, e.g. ascertaining mass flow rates and/or totalled mass flows, etc., for example, also circuit technologies according to the initially mentioned state of the art. According to an additional embodiment of the invention, the measuring, and evaluating, circuit μC is accordingly also provided by means of a microcomputer in the measuring device electronics ME, for example, a microcomputer implemented by means of a digital signal processor (DSP), and by means of program code correspondingly implemented and running therein. The program code can be stored persistently e.g. in a non-volatile memory EEPROM of the microcomputer and, in the case of the starting of the same loaded into a volatile memory RAM, e.g. integrated in the microcomputer. Suitable processors for such applications are e.g. those of type TMS320VC33 of the firm, Texas Instruments Inc. Of course, the primary signals s1, s2, s3, s4, must, for processing in the microcomputer, such as already indicated, be converted into corresponding digital signals by means of corresponding analog to digital converters A/D of the measuring device electronics ME; compare, for this, for example, the initially mentioned U.S. Pat. Nos.

6,311,136 or 6,073,495 or also the aforementioned measurement transmitters of the series "PROMASS 83".

The measuring, and evaluating, circuit μC serves, according to an embodiment of the invention, especially, by means of the at least three primary signal s1, s2 s3 delivered by the sensor arrangement 50, for example, on the basis of a phase difference detected between the primary signals s1, s2 the first and second oscillation sensor 51, 52 generated in the case of measuring tube 10 oscillating partially in the wanted, and Coriolis, modes and/or on the basis of a phase difference detected between the primary signals s1, s3 of the first and third oscillation sensor 51, 53 generated in the case of the measuring tube 10 oscillating partially in the wanted, and Coriolis, modes, to ascertain, recurringly, a measured value of mass flow $X_m$, which represents, exactly as possible, the mass flow rate, m, to be measured for medium being guided through the measuring transducer. Alternatively thereto or in supplementation thereof, the measuring, and evaluating, circuit serves, for example, derived from a current mass flow rate value $X_m$ and/or a plurality of earlier sequentially produced and/or measured values of mass flow flow rate, for ascertaining a mass measured value $X_M$, which represents, instantaneously, a totalled mass flow, M, integrated over time. For the mentioned case, in which the sensor arrangement 50 is formed also by means of four oscillation sensors, the evaluating circuit can generate the measured value of mass flow $X_m$ supplementally also with application of the fourth primary signal s4.

For such purpose, the evaluating circuit, according to an additional embodiment of the invention, produces, during operation, recurringly, a phase difference value $X^I_{\Delta\phi}$ of first type, which represents, instantaneously, the phase difference, $\Delta\phi^I$, existing between the first primary signal s1 and the second primary signal s2. In supplementation thereof, the evaluating circuit, according to an additional embodiment of the invention, produces during operation, recurringly, a phase difference value $X^{II}_{\Delta\phi}$ of second type, which represents, instantaneously, the phase difference, $\Delta\phi^{II}$, type existing between the third primary signal s3 and another of the primary signal delivered by the sensor arrangement—here thus the first or second primary signal s1, s2, or the, in given cases, likewise delivered, fourth primary signal s4. Additionally, the evaluating circuit generates the measured value of mass flow $X_m$ by means of the phase difference value $X^I_{\Delta\phi}$ of first type and by means of the phase difference value $X^{II}_{\Delta\phi}$ of second type, for example, based on the formula:

$$X_m = \frac{A^I \cdot (K^{II}_1 \cdot X^{II}_{\Delta\phi} - K^{II}_0) - A^{II} \cdot (K^I_1 \cdot X^I_{\Delta\phi} - K^I_0)}{A^I - A^{II}} \quad (1)$$

The measuring system parameters $A^I$, $A^{II}$, $K^I_0$, $K^I_1$, $K^{II}_0$, $K^{II}_1$ appearing in Eq. (1) and characterizing the measuring system of the invention in greater detail are defined as follows:

$K^I_0$ A measuring system parameter, for example, an experimentally earlier ascertained and/or internally stored, measuring system parameter, which represents a first zero point, $ZERO^I$, of the measuring system;

$K^I_1$ A measuring system parameter, for example, an experimentally earlier ascertained and/or internally stored, measuring system parameter, which represents a first sensitivity, $SPAN^I$, of the measuring system;

$K^{II}_0$ A measuring system parameter, for example, an experimentally earlier ascertained and/or internally stored, measuring system parameter, which represents a second zero point, $ZERO^{II}$, of the measuring system;

$K^{II}_1$ A measuring system parameter, for example, an experimentally earlier ascertained and/or internally stored, measuring system parameter, which represents a second sensitivity, $SPAN^{II}$, of the measuring system;

$A^I$ A measuring system parameter, for example, an experimentally earlier ascertained and/or internally stored, measuring system parameter, which represents a relative pressure dependence, $PRESSURE^I$, of the first sensitivity, $SPAN^I$, of the measuring system, especially a relative pressure dependence referenced to the first sensitivity, $SPAN^I$, of the measuring system; and $A^{II}$ A measuring system parameter, for example, an experimentally earlier ascertained and/or internally stored, measuring system parameter, which represents a relative pressure dependence, $PRESSURE^{II}$, of the second sensitivity, $SPAN^{II}$, of the measuring system, especially a relative pressure dependence referenced to the second sensitivity, $SPAN^{II}$, of the measuring system.

DES.

In such case, the first zero point, $ZERO^I$, of the measuring system, or the measuring system parameter $K^I_0$ representing this, corresponds to a phase difference, $\Delta\phi^I_0$, measured between the first primary signal s1 and the second primary signal s2 in the case of medium standing in the measuring tube, i.e. $m_{DESIRED}=0$, or to a phase difference calculated between the first primary signal s1 and the second primary signal s2 for medium standing in the measuring tube. For example, the measuring system parameter $K^I_0$ representing the first zero point, $ZERO^I$, of the measuring system can be ascertained based on the formula:

$$K^I_0 = X^I_{m,0} \sim X^I_{\Delta\phi,0} = \Delta\phi^I_0 (\rightarrow m_{DES.}=0) \quad (2)$$

or at least in a manner fulfilling this for the particular measuring system. In manner analogous thereto, the second zero point, $ZERO^{II}$, of the measuring system, or the measuring system parameter $K^{II}_0$ representing this, corresponds to a phase difference, $\Delta\phi^{II}_0$, measured between the third primary signal s3 and another of the of the sensor arrangement delivered primary signals s2, s1, or s4 in the case of medium standing in the measuring tube, $m_{DESIRED}=0$, or to a phase difference calculated between the third primary signal s1 and the said other primary signal for medium standing in the measuring tube. For example, the measuring system parameter $K^{II}_0$ representing the second zero point, $ZERO^{II}$, of the measuring system can be ascertained based on the formula:

$$K^{II}_0 = X^{II}_{m,0} \sim X^{II}_{\Delta\phi} = \Delta\phi^{II}_0 (\rightarrow m_{DES.}=0) \quad (3)$$

or at least in a manner fulfilling this for the particular measuring system.

Additionally, the first sensitivity, $SPAN^I$, of the measuring system, or the measuring system parameter $K^I_1$ representing this, corresponds to a phase difference, $\Delta\phi^I_1$, measured between the first primary signal s1 and the second primary signal s2, for example, in the form of a phase difference value $X^I_{\Delta\phi}$ of first type correspondingly generated by means of the measuring system itself, in the case of supplying the measuring transducer with a flowing medium of known mass flow rate, $m_{DESIRED} < >0$. For example, the measuring system parameter $K^I_1$ representing the first sensitivity, $SPAN^I$, of the measuring system can be ascertained based on the formula:

$$K_1^I = \frac{m_{DES.} + K_0^I}{\Delta\varphi_1^I} = \frac{m_{DES.} + K_0^I}{X_{\Delta\varphi}^I} \quad \left(\to m_{\cdots DES.} <> 0\right) \quad (4)$$

or at least in a manner fulfilling this for the particular measuring system. In manner analogous thereto, the second sensitivity, $SPAN^{II}$, of the measuring system, or the measuring system parameter $K_1^{II}$ representing this, corresponds to a phase difference, $\Delta\varphi_1^{II}$, measured between the third primary signal s3 and another of the primary signals s1, s3, or s4 delivered by the sensor arrangement 50, for example, in the form of a phase difference value $X_{\Delta\varphi}^{II}$ of second type correspondingly generated by means of the measuring system itself, in the case of supplying the measuring transducer with a flowing medium of known mass flow rate, $m_{DESIRED} <> 0$. For example, the measuring system parameter $K_1^I$ representing the second sensitivity, $SPAN^{II}$, of the measuring system can be ascertained based on the formula:

$$K_1^{II} = \frac{m_{DES.} + K_0^{II}}{\Delta\varphi_1^{II}} = \frac{m_{DES.} + K_0^{II}}{X_{\Delta\varphi}^{II}} \quad \left(\to m_{\cdots DES/} <> 0\right) \quad (5)$$

or at least in a manner fulfilling this for the particular measuring system.

Finally, the pressure dependence, $PRESSURE^I$, of the first sensitivity, $SPAN^I$, of the measuring system, or the measuring system parameter $A^I$ representing this pressure dependence, $PRESSURE^I$, can be ascertained based on a phase difference, $\Delta\varphi_{p1}^I$, or $\Delta\varphi_{p2}^I$, in the case of supplying the measuring transducer with a flowing medium of known first average static pressure, $p_{DESIRED1}$, as well as thereafter with a flowing medium of known second average static pressure, $p_{DESIRED2}$, in each case, measured between the first primary signal s1 and the second primary signal s2, for example, also with application of the evaluating circuit directly in the measuring system. For example, the measuring system parameter $A^I$ representing the pressure dependence, $PRESSURE^I$, of the first sensitivity, $SPAN^I$, of the measuring system can be ascertained based on the formula:

$$A^I = \frac{K_1^I \cdot (\Delta\varphi_{p2}^I - \Delta\varphi_{p1}^I)}{p_{DES,2} \cdot (K_1^I \cdot \Delta\varphi_{p1}^I - K_0^I) - p_{DES;1} \cdot (K_1^I \cdot \Delta\varphi_{p2}^I - K_0^I)} \quad (6)$$

or at least in a manner fulfilling this for the particular measuring system. In manner analogous thereto, also the pressure dependence, $PRESSURE^{II}$, of the second sensitivity, $SPAN^{II}$, of the measuring system, or the measuring system parameter $A^{II}$ representing this pressure dependence, $PRESSURE^{II}$, can be ascertained based on a phase difference $\Delta\varphi_{p1}^{II}$, or $\Delta\varphi_{p2}^{II}$, in the case of supplying the measuring transducer with a flowing medium of known first average static pressure, $p_{DESIRED1}$, as well as after with a flowing medium of known second average static pressure, $p_{DESIRED2}$, in each case, measured between the third primary signal s3 and another of the primary signals s1, s2, s4, in each case, for example, also with application of the evaluating circuit directly in the measuring system. For example, the measuring system parameter $A^{II}$ representing the pressure dependence, $PRESSURE^{II}$, of the second sensitivity, $SPAN^{II}$, of the measuring system can be ascertained based on the formula:

$$A^{II} = \frac{K_1^{II} \cdot (\Delta\varphi_{p2}^{II} - \Delta\varphi_{p1}^{II})}{p_{DES,2} \cdot (K_1^{II} \cdot \Delta\varphi_{p1}^{II} - K_0^{II}) - p_{DES;1} \cdot (K_1^{II} \cdot \Delta\varphi_{p2}^{II} - K_0^{II})} \quad (7)$$

or at least in a manner fulfilling this for the particular measuring system.

The actual, or known mass flow rates, $m_{DESIRED}$, in each case, required for ascertaining the measuring system parameters $K_1^I$, $K_1^{II}$, representing the sensitivities of the measuring system and, in given cases, also for ascertaining the measuring system parameters $K_0^{II}$, $K_0^I$, representing the zero points of the measuring system or the measuring system parameters $A^I$, $A^{II}$, representing the pressure dependencies of the sensitivities of the measuring system can be ascertained sufficiently precisely, directly and correspondingly, for example, impressed by means of appropriately adjusted, medium providing pumps and/or, for example, also by means of a reference, mass flow measuring device in the course of a wet calibrating of the measuring system. Equally, also the actual, or known average static pressures, $p_{DESIRED1}$, $p_{DESIRED2}$, in each case, required for the measuring system parameter $A^I$, $A^{II}$ representing pressure dependencies of the sensitivities of the measuring system, can be ascertained directly and correspondingly, for example, impressed by means of correspondingly adjusted pumps and/or, for example, also by means of a reference, pressure measuring device in the course of a wet calibrating of the measuring system.

For ascertaining further measured values representing measured variables of the medium different from the mass flow, m, such as, for instance, the density, $\rho$, or viscosity, $\eta$, it can be quite of advantage, when the evaluating circuit of the measuring device electronics ME, already before the output of the ultimate, precise measured value of mass flow $X_m$, although not so exactly, however, with greater speed, delivers measured values, which, in each case, interimly and/or not sufficiently exactly, represent a mass flow rate, m, of medium flowing through the measuring transducer.

Therefore, according to an additional embodiment of the invention, it is additionally provided, that the evaluating circuit, by means of the first primary signal s1 as well as at least one other of the primary signals s2, s3, s4 of the measuring transducer, for example, thus the second primary signal, produces a provisional measured value, especially a digital, provisional measured value, of mass flow $X_m^I$ of first type, which represents, interimly and/or not sufficiently exactly, a mass flow rate, m, of medium flowing through the measuring transducer. This provisional measured value of mass flow $X_m^I$ of first type can result e.g. based on a phase difference, $\Delta\varphi^I$, existing between the first primary signal s1 and the second primary signal s2, insofar, thus also with application of the phase difference value $X_{\Delta\varphi}^I$ of first type in any event present in the evaluating circuit, as well as with application of the—likewise already present—measuring system parameters $K_0^I$, $K_1^I$, representing the first zero point, $ZERO^I$, or the first sensitivity, $SPAN^I$, of the measuring system. In keeping with this, according to an additional embodiment of the invention, the evaluating circuit is configured in such a manner, that it ascertains a provisional measured value of mass flow $X_m^I$ of first type based on the formula:

$$X_m^I = K_1^I \cdot X_{\Delta\varphi}^I - K_0^I \quad (8)$$

or at least in a manner fulfilling this. Insofar, the measuring system parameter $K_0^I$ representing the first zero point, $ZERO^I$, of the measuring system corresponds, conversely, thus also to a provisional measured value of mass flow $X_{m,0}^I$ of first type ascertained in the case of medium standing in the measuring tube, i.e. $m_{DESIRED}=0$.

Alternatively or in supplementation, according to an additional embodiment of the invention, it is additionally provided, that the evaluating circuit also, by means of the third primary signal s3 as well as at least one other of the primary signals s2, s3, s4 of the measuring transducer, for example, thus the first primary signal and/or the second primary signal, produces a provisional measured value, especially a digital, provisional measured value, of mass flow $X^{II}_m$ of second type, which represents, interimly and/or not sufficiently exactly, an instantaneous mass flow rate, m, of medium flowing through the measuring transducer.

The provisional measured value of mass flow $X^{II}_m$ of second type can result correspondingly based on a phase difference, $\Delta\phi^{II}$, existing between the third primary signal s3 and another of the primary signals s1, s2, s4, insofar, thus also with application of the phase difference value $X^{II}_{\Delta\phi}$ of second type in any event present in the evaluating circuit, as well as with application of the—likewise already present—measuring system parameters $K^{II}_0$, $K^{II}_1$ representing the second zero point, $ZERO^{II}$, and the second sensitivity, $SPAN^{II}$, of the measuring system, respectively. In keeping with this, according to an additional embodiment of the invention, the evaluating circuit is configured in such a manner, that it ascertains a provisional measured value of mass flow $X^{II}_m$ of second type based on the formula:

$$X^{II}_m = K^{II}_1 \cdot X^{II}_{\Delta\phi} - K^{II}_0 \qquad (9)$$

or at least in a manner fulfilling this. As a result, thus the measuring system parameter $K^{II}_0$ representing the second zero point, $ZERO^{II}$, of the measuring system corresponds, conversely, also to a provisional measured value of mass flow $X^{II}_{m,0}$ of second type ascertained in the case of medium standing in the measuring tube, i.e. $m_{DESIRED}=0$.

Equally as the two zero points, $ZERO^I$, $ZERO^{II}$, of the measuring system, also the two aforementioned measuring system parameters, $A^I$, $A^{II}$, representing the pressure dependencies, $PRESSURE^I$, or $PRESSURE^{II}$, of the sensitivity, $SPAN^I$, or $SPAN^{II}$, of the measuring system can be ascertained recurringly during operation on the basis of the provisional measured values of mass flows, in given cases, also in the case of a re-calibrating undertaken on the installed measuring system on-site and/or in connection with external pressure sensors installed within the pipeline system, for instance, based on the following formulas:

$$A^I = \frac{X^I_{m,p2} - X^I_{m,p1}}{p_{DES,2} \cdot X^I_{m,p1} - p_{DES,1} \cdot X^I_{m,p2}} \qquad (10)$$

$$A^{II} = \frac{X^{II}_{m,p2} - X^{II}_{m,p1}}{p_{DES,2} \cdot X^{II}_{m,p1} - p_{DES,1} \cdot X^{II}_{m,p2}}. \qquad (11)$$

In advantageous manner, the evaluating circuit can even also generate the measured value of mass flow $X_m$ by means of the instantaneously present, provisional measured value of mass flow $X^I_m$ of first type as well as by means of the instantaneously present, provisional measured value of mass flow $X^{II}_m$ of second type. This can be implemented in simple manner in the evaluating circuit by corresponding evaluation e.g. of the formula:

$$X_m = \frac{A^I \cdot X^{II}_m - A^{II} \cdot X^I_m}{A^I - A^{II}} \qquad (12)$$

Alternatively or in supplementation to the above-described, intrinsically pressure compensated and, insofar, highly accurate ascertaining of the measured value of mass flow, the evaluating circuit of the measuring system of the invention can additionally also be used for measuring pressure per se and for producing corresponding, validated pressure measured values on the basis of the at least three primary signal s1, s2, s3 delivered by means of the sensor arrangement. Accordingly, the evaluating circuit generates during operation, according to a variant of the measuring system of the invention, at least at times, both by means of the first primary signal s1, as well as also by means of the second primary signal s2 as well as by means of the third primary signal s3, for example, based on a phase difference existing between the first primary signal s3 and the second primary signal s2 and/or based on a phase difference existing between the first primary signal s3 and the third primary signal s3, a pressure measured value $X_p$, especially a digital, pressure measured value $X_p$, which represents, instantaneously a pressure, p, in medium flowing through the measuring transducer, especially a static pressure reigning in the at least one measuring tube. The ascertaining of a current pressure measured value $X_p$ in the evaluating circuit can occur in simple manner with application both of a current phase difference value $X^I_{\Delta\phi}$ of first type as well as also of a current phase difference value $X^{II}_{\Delta\phi}$ of second type, for instance, based on the formula:

$$X_p = \frac{(K^I_1 \cdot X^I_{\Delta\phi} - K^I_0) - (K^{II}_1 \cdot X^{II}_{\Delta\phi} - K^{II}_0)}{A^I \cdot (K^{II}_1 \cdot X^{II}_{\Delta\phi} - K^{II}_0) - A^{II} \cdot (K^I_1 \cdot X^I_{\Delta\phi} - K^I_0)}. \qquad (13)$$

Alternatively thereto or in supplementation thereof, the evaluating circuit can ascertain the measured value of pressure $X_p$, however, also by means of the provisional measured value of mass flow $X^I_m$ of first type and by means of the provisional measured value of mass flow $X^{II}_m$ of second type, for instance, based on the formula:

$$X_p = \frac{X^I_m - X^{II}_m}{A^I \cdot X^{II}_m - A^{II} \cdot X^I_m}. \qquad (14)$$

Additionally, the evaluating circuit of the measuring system of the invention can also serve, in manner known, per se, to those skilled in the art, supplementally to generate a density measured value $X_\rho$, which represents, instantaneously, a density, $\rho$, to be measured for the medium, such being derived from, for example, an oscillation frequency of lateral bending oscillations of the at least one measuring tube 10, for example, also those bending oscillations in the wanted mode, measured on the basis of at least one of the primary signals delivered from the sensor arrangement. Alternatively thereto or in supplementation thereof, the evaluating circuit can, such as quite usual in the case of in-line measuring devices of the type being discussed, in given cases, also be used to ascertain, derived from the driver signal $i_{exc}$, which, as is known, also can serve as a measure for an apparent viscosity or also for a viscosity, density product of the medium guided in the measuring tube, a viscosity measured value $X_\eta$, which represents, instantaneously, a viscosity of the medium; compare, for this, also U.S. Pat. Nos. 7,017,424, 6,840,109 or 6,651,513.

@Moreover, it can, however, also be directly assumed, that measured values, especially also possibly provisional, measured values ascertained by means of the measuring device electronics can be at least temporarily interimly stored in the measuring device electronics ME, for example, in the mentioned EEPROM-memory and/or RAM-memory, and so can be held sufficiently long for subsequent uses. The aforementioned calculational functions, especially also those serving for producing the measured value(s) of mass flow $X_m$ and/or the measured value of pressure $X_p$, symbolized by the formulas, Eqs. (1) to (14), can be evaluated very simply e.g. by means of the above mentioned microcomputer of the evaluating circuit µC or, for example, also one of therein correspondingly provided, digital signal processors DSP. The creation and implementing of corresponding algorithms, corresponding with the above-described formulas or, for example, also simulating the operation of the mentioned amplitude, or frequency, control circuit for the exciter mechanism, as well as their translation in the measuring device electronics into correspondingly executable program code is known, per se, to those skilled in the art and needs, consequently, —, in any event, with knowledge of the present invention—no detailed explanation. Of course, the aforementioned formulas, or other with the measuring device electronics implemented functionalities of the measuring system, can also be directly completely or partially implemented in the measuring device electronics ME by means of corresponding discretely constructed and/or hybrid, thus mixed analog, digital, calculational circuits.

The invention claimed is:

1. A measuring system, for flowable, especially fluid, media, said measuring system comprising:
   a measuring transducer, through which a medium flows during operation, at least at times, and which generates primary signals influenced by at least one measured variable characterizing the flowing medium; and
   an evaluating circuit electrically coupled with said measuring transducer and processing primary signals delivered by said measuring transducer as measured values, said measuring transducer includes:
   at least one measuring tube, vibrating, at least at times, during operation and serving for conveying medium to be measured;
   an exciter mechanism including at least one oscillation exciter, acting on said at least one measuring tube for causing said at least one measuring tube to vibrate; and
   a sensor arrangement serving for registering oscillations of said at least one measuring tube, said sensor arrangement including:
   a first oscillation sensor, arranged on said at least one measuring tube, spaced from said at least one oscillation exciter, for delivering a first primary signal of said measuring transducer representing vibrations of said measuring tube;
   a second oscillation sensor, arranged on said at least one measuring tube, spaced from said first oscillation sensor, and spaced from said at least one oscillation exciter for delivering simultaneously with the first primary signal, a second primary signal of said measuring transducer representing vibrations of said measuring tube;
   a third oscillation sensor, arranged on said measuring tube, spaced both from said first and said second oscillation sensors and spaced from said at least one oscillation exciter, for delivering, a third primary signal of said measuring transducer representing vibrations of said measuring tube and
   a fourth oscillation sensor, arranged on said measuring tube, spaced from said first, second and third oscillation sensors and spaced from said at least one oscillation exciter, for delivering, a fourth primary signal of said measuring transducer representing vibrations of said measuring tube, wherein:
   said evaluating circuit is adapted to generate, by means of said first, second third, and fourth primary signals, a measured value, which represent, a mass flow rate, of medium flowing through said measuring transducer.

2. The measuring system as claimed in claim 1, wherein:
said third oscillation sensor is placed on a measuring tube segment of said measuring tube extending between said first oscillation sensor and said at least one oscillation exciter.

3. The measuring system as claimed in claim 1, wherein:
at least said third oscillation sensor and said fourth oscillation sensor are of equal construction relative to one another.

4. The measuring system as claimed in claim 1, wherein:
said third oscillation sensor is arranged on the inlet side and said fourth oscillation sensor on the outlet side of said at least one measuring tube.

5. The measuring system as claimed in claim 1, wherein:
said third oscillation sensor and said fourth oscillation sensor are so placed in said measuring transducer, that an amplitude of the third primary signal and an amplitude of the fourth primary signal are influenced in equal measure by an internal pressure reigning in said at least one measuring tube.

6. The measuring system as claimed in claim 1, wherein:
said fourth oscillation sensor is placed on a measuring tube segment of said measuring tube extending between said second oscillation sensor and said at least one oscillation exciter.

7. The measuring system as claimed in claim 1, wherein:
said evaluating circuit produces, recurringly, during operation a phase difference value of a first type, which represents, instantaneously, a phase difference, existing between the first primary signal and the second primary signal.

8. The measuring system as claimed in claim 7, wherein:
said evaluating circuit produces, recurringly, during operation a phase difference value of a second type, which represents, instantaneously, a phase difference, type existing between the third primary signal and another of the primary signals.

9. The measuring system as claimed in claim 8, wherein:
the phase difference value of the second type represents the phase difference, existing between the third primary signal and the fourth primary signal.

10. The measuring system as claimed in claim 1, wherein:
said evaluating circuit produces, by means of the first primary signal as well as at least one other of the primary signals of said measuring transducer, a provisional measured value of mass flow of a first type, said provisional measured value interimly and/or not sufficiently exactly representing a mass flow rate, of the medium flowing through said measuring transducer.

11. The measuring system as claimed in claim 10, wherein:
the evaluating circuit produces, recurringly, during operation a phase difference value of the first type, which represents, instantaneously, a phase difference, existing between the first primary signal and the second primary signal, and said evaluating circuit produces the provisional measured value of mass flow of a first type with the application of the phase difference value of a first type.

12. The measuring system as claimed in claim 10, wherein:
said evaluating circuit generates the provisional measured value of mass flow of a first type based on a phase difference, of the first type existing between the first primary signal and the second primary signal as well as with application of a measuring system parameter, representing a first zero point, of the measuring system and with application of a measuring system parameter, representing a first sensitivity, of the measuring system.

13. The measuring system as claimed in claim 12, wherein:
said evaluating circuit generates the provisional measured value of mass flow of a first type with application of the phase difference value of a first type as well as with application of the measuring system parameter representing the first zero point, of the measuring system and with application of the measuring system parameter representing the first sensitivity, of the measuring system.

14. The measuring system as claimed in claim 12, wherein:
the measuring system parameter representing the first zero point, of the measuring system corresponds to a phase difference, between the first primary signal and the second primary signal, measured in the case of a medium standing in said measuring tube; and/or in the measuring system parameter representing the first zero point, of the measuring system corresponds to a provisional measured value of mass flow of a first type ascertained in the case of a medium standing in the measuring tube.

15. The measuring system as claimed in claim 12, wherein:
the measuring system parameter representing the first sensitivity, of the measuring system, corresponds to a phase difference, measured between the first primary signal and the second primary signal in the case of supplying said measuring transducer with a known flowing medium, and supplying the measuring transducer with a flowing medium of impressed mass flow rate; and/or wherein the measuring system parameter representing the first sensitivity of the measuring system, corresponds to at least one of: a mass flow rate ascertained by means of a reference, mass flow measuring device, and a phase difference value of a first type ascertained in the case of supplying said measuring transducer with a flowing medium of known and/or impressed mass flow rate.

16. The measuring system as claimed in claim 15, wherein:
the measuring system parameter representing the first sensitivity, of the measuring system, corresponds to a phase difference, measured between the first primary signal and the second primary signal in the case of supplying said measuring transducer with a flowing medium also of known and/or impressed, average static pressure; and/or wherein the measuring system parameter representing the first sensitivity of the measuring system, corresponds to a phase difference value of the first type ascertained in the case of supplying the measuring transducer with a flowing medium of known and/or impressed, average static pressure.

17. The measuring system as claimed in claim 12, wherein:
said evaluating circuit generates the measured value of a mass flow with application of a measuring system parameter, representing a pressure dependence, of the first sensitivity, of the measuring system.

18. The measuring system as claimed in claim 10, wherein:
said evaluating circuit, by means of the third primary signal as well as at least one other of the primary signals of said measuring transducer, produces a provisional measured value of mass flow of the second type, said measured value interimly and/or not sufficiently exactly representing the mass flow rate, of the medium flowing through said measuring transducer.

19. The measuring system as claimed in claim 18, wherein:
said evaluating circuit generates the provisional measured value of mass flow of the second type both by means of the third primary signal as well as also by means of the fourth primary signal.

20. The measuring system as claimed in claim 19, wherein:
the evaluating circuit produces, recurringly, during operation a phase difference value of first type, which represents, instantaneously, a phase difference, existing between the first primary signal and the second primary signal; and said evaluating circuit generates the provisional measured value of mass flow of a second type based on a phase difference, of a second type existing between the third primary signal and another of the primary signals, as well as with application of a measuring system parameter, representing a second zero point, of the measuring system and with application of a measuring system parameter, representing a second sensitivity, of the measuring system.

21. The measuring system as claimed in claim 20, wherein:
said evaluating circuit generates the provisional measured value of mass flow of a second type with application of the phase difference value of a second type as well as with application of the measuring system parameter representing the second zero point, of the measuring system and with application of the measuring system parameter representing the second sensitivity, of the measuring system.

22. The measuring system as claimed in claim 21, wherein:
the measuring system parameter representing the second zero point, of the measuring system corresponds to a phase difference, measured between the third primary signal and another of the primary signals in the case of a medium standing in said measuring tube; and/or the measuring system parameter representing the second zero point, of the measuring system corresponds to a provisional measured value of mass flow of a second type ascertained in the case of a medium standing in said measuring tube.

23. The measuring system as claimed in claim 21, wherein:
said evaluating circuit generates the measured value of a mass flow by means of the provisional measured value of the mass flow of a first type and by means of the provisional measured value of mass flow of a second type.

24. The measuring system as claimed in claim 19, wherein:
said evaluating circuit generates the measured value of mass flow by means of the phase difference value of a first type and by means of the phase difference value of a second type.

25. The measuring system as claimed in claim 24, wherein:
said evaluating circuit generates the measured value of mass flow with application of a measuring system parameter, representing a pressure dependence, of the second sensitivity, of the measuring system.

26. The measuring system as claimed in claim 25, wherein:
the measuring system parameter representing the pressure dependence, of the first sensitivity, of the measuring system is ascertained based on a phase difference, measured between the first primary signal and the second primary signal in the case of supplying said measuring transducer with a flowing medium of known and/or impressed, first average static pressure, and based on a phase difference, measured between the first primary signal and the second primary signal in the case of supplying said measuring transducer with a flowing medium of known and/or impressed second average static pressure.

27. The measuring system as claimed in claim 26, wherein:
the evaluating circuit produces, by means of the first primary signal as well as at least one other of the primary signals of the measuring transducer a provisional measured value of mass flow of first type and/or not sufficiently exactly representing a mass flow rate, m, of medium flowing through the measuring transducer, and
the measuring system parameter representing the pressure dependence, of the first sensitivity, of the measuring system is ascertained based on a provisional measured value of a mass flow of a first type generated in the case of supplying said measuring transducer with a flowing medium of known and/or impressed, first average static pressure, and/or a first average static pressure, and based on a provisional measured value of mass flow of a first type generated in the case of supplying said measuring transducer with a flowing medium of known and/or impressed, second average static pressure.

28. The measuring system as claimed in claim 27, wherein:
the measuring system parameter representing the pressure dependence, of the second sensitivity, of the measuring system is ascertained based on a phase difference, measured between the third primary signal and another of the primary signals in the case of supplying said measuring transducer with a flowing medium of known and/or impressed, first average static pressure and based on a phase difference, measured between the third primary signal and another of the primary signals in the case of supplying said measuring transducer with a flowing medium of known and/or impressed, second average static pressure.

29. The measuring system as claimed in claim 28, wherein:
the measuring system parameter representing the pressure dependence, of the second sensitivity, of the measuring system is ascertained based on a provisional measured value of mass flow of a second type generated in the case of supplying said measuring transducer with a flowing medium of known and/or impressed, first average static pressure, and based on a provisional measured value of mass flow of a second type generated in the case of supplying said measuring transducer with a flowing medium of known and/or impressed, second average static pressure, and/or a second average static pressure, ascertained by means of a reference, pressure measuring device.

30. The measuring system as claimed in claim 1, wherein:
said evaluating circuit, at least at times, both by means of the first primary signal as well as also by means of the second primary signal as well as by means of the third primary signal, generates a pressure measured value, which, represents, instantaneously, a pressure, in the medium flowing through said measuring transducer.

31. The measuring system as claimed in claim 30, wherein:
the evaluating circuit produces recurringly during operation a phase difference value of second type, which represents a phase difference existing between the third primary signal and another of the primary signals, and
said evaluating circuit generates the measured value of pressure by means of the phase difference value of a first type and by means of the phase difference value of a second type.

32. The measuring system as claimed in claim 31, wherein:
the evaluating circuit produces, by means of the first primary signal as well as at least one other of the primary signals of the measuring transducer, a provisional measured value of mass flow of first type and, by means of the third primary signal as well as at least one other of the primary signals of the measuring transducer, a provisional measured value of mass flow of second type, each of said provisional measured values interimly and/or not sufficiently exactly representing a mass flow rate of medium flowing through the measuring transducer, and
said evaluating circuit ascertains the measured value of pressure by means of the provisional measured value of mass flow of a first type and by means of the provisional measured value of mass flow of a second type.

33. The measuring system as claimed in claim 1, wherein:
said first oscillation sensor and said third oscillation sensor are so placed in said measuring transducer, that an amplitude of the first primary signal is influenced in smaller measure by an average static pressure reigning instantaneously in said at least one measuring tube than is an amplitude of the third primary signal; and/or
said second oscillation sensor and said third oscillation sensor are so placed in said measuring transducer, that an amplitude of the second primary signal is influenced in smaller measure by an average static pressure reigning instantaneously in said at least one measuring tube than is an amplitude of the third primary signal; and/or
said first oscillation sensor and said second oscillation sensor are so placed in said measuring transducer, that an amplitude of the first primary signal and an amplitude of the second primary signal in equal measure are influenced by an average static pressure reigning instantaneously in said at least one measuring tube.

34. The measuring system as claimed in claim 1, wherein:
said at least one measuring tube is embodied at least sectionally essentially with a V shape.

35. The measuring system as claimed in claim 1, wherein:
said at least one measuring tube is embodied at least sectionally essentially in a U shape.

36. The measuring system as claimed in claim 1, wherein:
at least said first oscillation sensor and said second oscillation sensor are of equal construction relative to one another.

37. The measuring system as claimed in claim 1, wherein:
at least said first oscillation sensor and said third oscillation sensor are of equal construction relative to one another.

38. The measuring system as claimed in claim 1, wherein:
said first oscillation sensor is arranged on the inlet side and said second oscillation sensor on the outlet side of said at least one measuring tube.

39. The measuring system as claimed in claim 1, wherein:
said at least one measuring tube includes an essentially freely oscillating, measuring tube segment, extending between an end of said measuring tube defining an inlet-side, oscillation node of oscillations of said measuring tube and an end of said measuring tube defining an outlet-side, oscillation node of oscillations.

40. The measuring system as defined in claim 39, wherein:
both said first oscillation sensor, as well as also said second oscillation sensor, as well as also said third oscillation sensor are so placed in said measuring transducer, that each of the three oscillation sensors, register vibrations of the essentially freely oscillating, measuring tube segment.

41. The measuring system as claimed in claim 40, wherein:
said at least one measuring tube is during operation excited by means of said exciter mechanism, at least at times, in a wanted mode, in which it, executes bending oscillations, about an imaginary oscillation axis.

42. The measuring system as claimed in claim 41, wherein:
each of the at least four primary signals, of said measuring transducer includes, in each case, a signal component with a signal frequency corresponding to the bending oscillations in the wanted mode and/or to a resonance frequency, of the at least one measuring tube.

43. The measuring system as claimed in claim 1, further comprising:
a driver circuit electrically coupled with said measuring transducer and delivering at least one exciter signal controlling its exciter mechanism.

44. The measuring system as claimed in claim 1, further comprising:
a counteroscillator affixed on the inlet side of said measuring tube to form a first coupling zone and affixed on the outlet side of said measuring tube to form a second coupling zone.

45. The measuring system as claimed in claim 44, wherein:
said first, second and third oscillation sensors, are so placed in said measuring transducer, that each of the three oscillation sensors register oscillations of the at least one measuring tube relative to said counteroscillator.

46. The measuring system as claimed in claim 45, wherein:
said fourth oscillation sensor is so placed in said measuring transducer, that it registers oscillations of said at least one measuring tube relative to said counteroscillator.

47. The measuring system as claimed in claim 46, wherein:
said measuring tube and said counteroscillator oscillate during operation at least at a shared oscillation frequency with opposite phase relative to one another; and/or wherein the first, the second, and the third primary signals represent oscillatory movements, of said at least one measuring tube relative to said counteroscillator.

48. The measuring system as claimed in claim 46, wherein:
the fourth primary signal represents oscillatory movements, of said at least one measuring tube relative to said counteroscillator.

49. The measuring system as claimed in claim 46, wherein:
said oscillation sensors, register vibrations of said at least one measuring tube, and said counteroscillator.

50. The measuring system as claimed in claim 1, wherein:
said evaluating circuit generates, at least at times, by means of at least one of the primary signals, a density measured value, which represents, instantaneously, a density, of the medium flowing through said measuring transducer.

51. The measuring system as claimed in claim 1, wherein:
said evaluating circuit generates, at least at times, by means of at least one of the primary signals, a viscosity measured value, which represents a viscosity, of the medium flowing through said measuring transducer.

52. The use of a measuring system according to claim 1 for measuring a mass flow, a density, a viscosity, and a pressure of a medium flowing in a process line.

* * * * *